(12) United States Patent
Nguyen et al.

(10) Patent No.: US 12,419,833 B2
(45) Date of Patent: Sep. 23, 2025

(54) INJECTABLE TRIAMCINOLONE FORMULATIONS

(71) Applicant: CLEARSIDE BIOMEDICAL, INC., Alpharetta, GA (US)

(72) Inventors: Thai Q Nguyen, Alpharetta, GA (US); Brian Burke, Alpharetta, GA (US); Edward Lee, Alpharetta, GA (US); Rafael Victor Andino, Alpharetta, GA (US)

(73) Assignee: CLEARSIDE BIOMEDICAL, INC., Alpharetta, GA (US)

( * ) Notice: Subject to any disclaimer, the term of this patent is extended or adjusted under 35 U.S.C. 154(b) by 0 days.

(21) Appl. No.: 17/603,816

(22) PCT Filed: Apr. 16, 2020

(86) PCT No.: PCT/US2020/028493
§ 371 (c)(1),
(2) Date: Oct. 14, 2021

(87) PCT Pub. No.: WO2020/214799
PCT Pub. Date: Oct. 22, 2020

(65) Prior Publication Data
US 2022/0211618 A1 Jul. 7, 2022

Related U.S. Application Data

(60) Provisional application No. 62/834,554, filed on Apr. 16, 2019.

(51) Int. Cl.
| | | |
|---|---|---|
| *A61K 9/10* | (2006.01) | |
| *A61K 9/00* | (2006.01) | |
| *A61K 31/58* | (2006.01) | |
| *A61K 47/02* | (2006.01) | |
| *A61K 47/26* | (2006.01) | |
| *A61K 47/38* | (2006.01) | |
| *A61M 5/32* | (2006.01) | |

(52) U.S. Cl.
CPC .............. *A61K 9/10* (2013.01); *A61K 9/0019* (2013.01); *A61K 9/0048* (2013.01); *A61K 31/58* (2013.01); *A61K 47/02* (2013.01); *A61K 47/26* (2013.01); *A61K 47/38* (2013.01); *A61M 5/32* (2013.01)

(58) Field of Classification Search
CPC ...... A61K 9/10; A61K 9/0019; A61K 9/0048; A61K 31/58; A61K 47/02; A61K 47/26; A61K 47/38; A61K 9/14; A61M 5/32; A61P 27/02
See application file for complete search history.

(56) References Cited

U.S. PATENT DOCUMENTS

| | | | |
|---|---|---|---|
| 5,023,087 | A | 6/1991 | Yau-Young |
| 8,128,960 | B2 | 3/2012 | Kabra et al. |
| 2004/0186084 | A1* | 9/2004 | Alam ..................... A61K 47/26 |
| | | | 514/174 |
| 2010/0256597 | A1 | 10/2010 | Prausnitz et al. |
| 2011/0243999 | A1 | 10/2011 | Dellamary et al. |
| 2013/0065888 | A1* | 3/2013 | Cetina-Cizmek .... A61K 31/542 |
| | | | 514/226.5 |
| 2015/0258120 | A1 | 9/2015 | Zarnitsyn et al. |
| 2015/0297609 | A1 | 10/2015 | Shah et al. |
| 2017/0112665 | A1 | 4/2017 | Andino et al. |
| 2017/0216228 | A1 | 8/2017 | Asgharian et al. |
| 2018/0028516 | A1 | 2/2018 | Zarnitsyn et al. |
| 2018/0042765 | A1 | 2/2018 | Noronha et al. |

FOREIGN PATENT DOCUMENTS

| | | | | |
|---|---|---|---|---|
| CN | 101959519 | A | 1/2011 | |
| CN | 106794321 | A | 5/2017 | |
| KR | 20100127267 | A | 12/2010 | |
| KR | 20150013158 | A | 2/2015 | |
| WO | WO-2009114521 | A1 * | 9/2009 | ............. A61K 31/58 |
| WO | WO-2013169647 | A1 | 11/2013 | |
| WO | WO-2015196085 | A2 | 12/2015 | |
| WO | WO-2020214799 | A1 | 10/2020 | |

OTHER PUBLICATIONS

Chitnis et al. (A resistance-sensing mechanical injector for the precise delivery of liquids to target tissue, published online Feb. 25, 2019 (Year: 2019).*
International Search Report and Written Opinion for International Application No. PCT/US2020/028493, dated Jul. 15, 2020, 10 pages.
Mansoor, S. et al., "Pharmacokinetics and Biodistribution of Triamcinolone Acetonide Following Suprachoroidal Injection into the Rabbit Eye In Vivo Using a Microneedle," Investigative Ophthalmology & Visual Science, ARVO Annual Meeting Abstract, Apr. 2011, vol. 52, 6585, 2 pages.
Extended European Search Report for European Application No. EP20791438.3, dated Nov. 14, 2022, 10 Pages.
Office Action and Search Report for China Application No. CN202080043050.1, dated Sep. 28, 2023, 25 pages.
Office Action and Search Report for Taiwan Application No. TW20200112879, dated Dec. 5, 2023, 7 pages.
Office Action for India Application No. IN202117052224, dated Jun. 23, 2023, 9 pages.
Aref et al., "Generic Drugs for the treatment of ocular conditions: changing the treatment landscape," Expert Reviews in Clinical Pharmacology, Sep. 1, 2014, vol. 7, No. 5, pp. 551-553.

(Continued)

*Primary Examiner* — Robert A Wax
*Assistant Examiner* — John Seungjai Kwon
(74) *Attorney, Agent, or Firm* — COOLEY LLP

(57) ABSTRACT

The present disclosure relates to pharmaceutical suspensions of triamcinolone acetonide, methods of producing such suspensions and methods of using of such suspensions. The pharmaceutical suspensions of the present disclosure are stable and suitable for administration by suprachoroidal injection through a 30-gauge microneedle.

26 Claims, 9 Drawing Sheets

(56) References Cited

OTHER PUBLICATIONS

Balci et al., "The importance of measuring intraocular pressure using a tonometer in order to estimate the postmortem interval, " The American journal of forensic medicine and pathology, Jun. 1, 2010, vol. 31, No. 2, pp. 151-155.
Chambers, "Ophthalmic Generics—Are They Really the Same?" Ophthalmology, Jun. 1, 2012, vol. 119, No. 6, pp. 1095-1096.
Chiang, B. et al., "Distribution of particles, small molecules and polymeric formulation excipients in the suprachoroidal space after microneedle injection," Experimental eye research, Dec. 1, 2016, vol. 153, pp. 101-109.
Choi et al., "Generic drug device combination products: Regulatory and scientific considerations," International Journal of Pharmaceutics, Jun. 15, 2018, vol. 544, No. 2, pp. 443-454.
Ciulla et al., "Microinjection via the Suprachoroidal Space: A Review of a Novel Mode of Administration," American Journal of Managed Care, Nov. 2, 2022, vol. 28, pp. S243-S252.
Clearside Boimedical, Inc. Xipere™ (triamcinolone acetonide injectable suspension) [package label]. U.S. Food and Drug Administration website. <https://www.accessdata.fda.gov/drugsatfda_docs/label/2021/211950Orig1s000correctedlbl.pdf>. Revised Jan. 22, 2021. Accessed Sep. 12, 2024.
Emi et al., "Hydrostatic Pressure of the Suprachoroidal Space," Investig. Ophthalmol. Vis. Sci, Feb. 1, 1989, vol. 30, No. 2, pp. 233-238.
Hancock et al., "Biomechanics of suprachoroidal drug delivery: from benchtop to clinical investigation in ocular therapies," Expert Opinion on Drug Delivery, Jun. 3, 2021, vol. 18, No. 6, pp. 777-788.
Hartman et al., "Intravitreal, subretinal, and suprachoroidal injections: evolution of microneedles for drug delivery," Journal of Ocular Pharmacology and Therapeutics, Mar. 1, 2018, vol. 34, Nos. 1-2, pp. 141-153.
Kansara et al., "Suprachoroidal delivery enables targeting, localization and durability of small molecule suspensions," Journal of Controlled Release, Sep. 1, 2022, vol. 349, pp. 1045-1051.
Kita, "Effects on retinal adhesive force in vivo of metabolically active agents in the subretinal space," Investigative Ophthalmology & Visual Science, May 1, 1992, vol. 33, No. 6, pp. 1883-1887.
Muya et al., "Suprachoroidal injection of triamcinolone acetonide suspension: ocular pharmacokinetics and distribution in rabbits demonstrates high and durable levels in the chorioretina," Journal of Ocular Pharmacology and Therapeutics, Aug. 1, 2022, vol. 38, No. 6, pp. 459-467.
Porter et al., "What is Macular Edema," American Academy of Ophthalmology, Apr. 27, 2023, located online at https://www.aao.org/eye-health/diseases/what-is-macular-edema, 3 pages.
Rai et al., "The suprachoroidal pathway: a new drug delivery route to the back of the eye," Drug Discovery Today, Apr. 1, 2015, vol. 20, No. 4, pp. 491-495.
Tucker, FDA Citizen Petition submitted by Bausch+Lomb, Nov. 30, 2023, 26 pages.
Wan et al., "Clinical Characterization of Suprachoroidal Injection Procedure Utilizing a Microinjector across Three Retinal Disorders," Transl. Vis. Sci. Technol., Oct. 1, 2020, vol. 9, No. 11, p. 27.

\* cited by examiner

INJECTABLE TRIAMCINOLONE FORMULATIONS

CROSS-REFERENCE TO RELATED APPLICATIONS

This application is a U.S. National Phase of International Application No. PCT/US2020/028493, filed Apr. 16, 2020, which claims priority to U.S. Application No. 62/834,554, filed Apr. 16, 2019, the contents of which are hereby incorporated by reference in their entirety.

FIELD OF THE DISCLOSURE

The present disclosure relates to injectable pharmaceutical suspensions containing triamcinolone acetonide and processes for preparing the same.

BACKGROUND OF THE DISCLOSURE

Triamcinolone acetonide is a synthetic corticosteroid with anti-inflammatory activity. TRIESENCE® is an FDA-approved triamcinolone acetonide suspension administered intravitreally by injection for the treatment of ocular disorders, including sympathetic ophthalmia, temporal arteritis, uveitis and ocular inflammatory conditions unresponsive to topical steroids.

The administration of suspensions by ocular injection presents numerous challenges. For example, the suspension product must be suitable for uniform product, stable for storage and, for administration, readily resuspendable/redispersible provide to a uniform suspension capable of delivery through a needle (preferably a microneedle) without clogging or the need to use excessive force in the injection. TRIESENCE® addresses these challenges with vigorous shaking and haste. Prior to administration, the TRIESENCE® product must be "vigorously shaken for 10 seconds before use to ensure a uniform suspension." (TRIESENCE® prescribing label, Section 2.3 Preparation for Administration). The instructions further provide that "TRIESENCE® should be injected without delay to prevent settling in the syringe."

Therefore, there is a need for stable and readily resuspendable/redispersible triamcinolone acetonide-containing suspensions that are suitable for ocular injection.

The present disclosure provides advantageous triamcinolone acetonide-containing suspensions that readily are resuspendable/redispersible and, in compliance with recent regulatory guidelines, are essentially free of visible particulate matter that is not related to the triamcinolone acetonide active ingredient.

SUMMARY OF THE DISCLOSURE

The present disclosure provides a triamcinolone acetonide suspension with improved physical parameters (such as essentially aggregate-free, essentially particulate-free, viscosity, degree of flocculation and settling times) such that the suspensions may be packaged in a suitable container with consistent triamcinolone acetonide weights and assays in each container. The triamcinolone acetonide suspensions of the present disclosure are well suited for ocular injection, especially to the posterior region of the eye by suprachoroidal injection.

In one aspect, the present disclosure provides essentially particulate-free and aggregate-free pharmaceutical suspensions of triamcinolone acetonide. In such embodiments, the pharmaceutical suspensions of triamcinolone acetonide are essentially free of visible (e.g., particles greater than about 100 μm), foreign particles (i.e., particulate matter that are not related to the triamcinolone acetonide active ingredient) as determined by the methods described herein. Furthermore, in such embodiments, the pharmaceutical suspensions of triamcinolone acetonide are essentially free of aggregated triamcinolone acetonide particles (or aggregates) as determined by the methods described herein.

In some embodiments, the disclosure provides triamcinolone acetonide suspensions comprising:
  (a) about 40 mg/mL of triamcinolone acetonide; and
  (b) a wetting agent;
  wherein the composition is essentially particulate-free and aggregate-free.

In one aspect, the present disclosure provides a pharmaceutical suspension prepared by a process comprising:
  (a) providing an essentially particulate-free first solution comprising one or more viscosity agents, one or more one tonicity agents, and one or more pH buffer agents in an aqueous solvent;
  (b) providing an essentially particulate-free second solution comprising one or more wetting agents in an aqueous solvent;
  (c) adding triamcinolone acetonide particles having a $D_{70}$ of less than about 5 μm to the solution of Step (b) to provide a suspension;
  (d) adding the suspension of Step (c) to the solution of Step (a); and
  (e) sonicating the suspension of Step (d),
  wherein the suspension comprises about 40 mg/mL of triamcinolone acetonide In some embodiments, the sonication Step (e) is conducted until the suspension is essentially aggregate-free. In some embodiments, the sonication Step (e) is conducted until the suspension is essentially aggregate-free as determined by a Syringeability Force Test described in Example 3. In some embodiments, the sonication Step (e) is conducted until the Syringeability Force Distribution ($D_f90$) of the suspension is not more than about 760 $g^f$ as determined by the Syringeability Force Test (i.e., the suspension is essentially aggregate-free).

In one aspect, the present disclosure provides pharmaceutical suspensions containing about 40 mg/mL of triamcinolone acetonide and a wetting agent, wherein the injection of the suspension through a 30 gauge needle of 900 μm to 1100 μm length provides an average glide force of less than about 1.00 Newton. In some embodiments, the composition is essentially particulate-free and aggregate-free. In some embodiments, the suspension is essentially particulate-free as determined by the visual inspection methods described in USP <790>. In some embodiments, the suspension is essentially particulate-free as determined by the destructive sample preparation and visual inspection methods described in USP <1790>.

The present disclosure also provides a method of preparing a pharmaceutical suspension comprising:
  (a) providing an essentially particulate-free first solution comprising one or more viscosity agents, one or more one tonicity agents, and one or more pH buffer agents in an aqueous solvent;
  (b) providing an essentially particulate-free second solution comprising one or more wetting agents in an aqueous solvent;
  (c) adding triamcinolone acetonide particles having a $D_{70}$ of less than about 5 μm to the solution of Step (b) to provide a suspension;

(d) adding the suspension of Step (c) to the solution of Step (a); and
(e) sonicating the suspension of Step (d),
wherein the suspension comprises about 40 mg/mL of triamcinolone acetonide.

In one aspect, the present disclosure provides triamcinolone acetonide suspensions prepared by a process comprising:
(a) heating a mixture of one or more wetting agents, one or more one tonicity agents, one or more pH buffer agents, and triamcinolone acetonide having a $D_{50}$ of less than about 5 μm in an aqueous solvent;
(b) cooling the suspension of Step (a);
(c) adding an aqueous solution of one or more viscosity agents to the suspension of Step (b);
(d) stirring the suspension of Step (c) at a low-shear stirring rate; and
(e) sonicating the suspension of Step (d),
wherein the suspension comprises about 40 mg/mL of triamcinolone acetonide.

In one aspect, the present disclosure provides pharmaceutical suspensions containing about 40 mg/mL of triamcinolone acetonide, wherein the average floc size (i.e., average particle size) of the triamcinolone acetonide is from about 80 μm to about 120 μm, and a wetting agent wherein the injection of the suspension through a 30 gauge needle of 1100 μm length provides an average glide force of less than about 1.30 Newton (N). In some embodiments, the suspensions comprise at least about 0.02% w/v of the wetting agent.

In one aspect, the present disclosure provides pharmaceutical suspensions containing about 40 mg/mL of triamcinolone acetonide and a wetting agent, wherein the injection of the suspension through a 30 gauge needle of 1100 μm length provides an average glide force of less than about 1.30 Newton (N) and degree of flocculation of the suspension is from about 15 to about 20. In some embodiments, the suspensions comprise at least about 0.02% w/v of the wetting agent.

In some embodiments, the wetting agent is polysorbate 80. In some embodiments, the suspension comprises about 0.02% w/v polysorbate 80. In some embodiments, the one or more tonicity agents comprises sodium chloride, potassium chloride, calcium chloride, and magnesium chloride. In some embodiments, the viscosity agent is carboxymethylcellulose sodium.

In one aspect, the present disclosure provides triamcinolone acetonide suspensions consisting essentially of:
(a) from about 0.35 to about 0.45 mg/mL of triamcinolone acetonide, wherein the average floc size (i.e., average particle size) of the triamcinolone acetonide is from about 80 μm to about 120 μm,
(b) from about 0.50% to about 0.60% of sodium chloride (% w/v),
(c) from about 0.4% to about 0.6% of carboxymethylcellulose sodium (% w/v),
(d) from about 0.01% to about 0.03% of polysorbate 80 (% w/v),
(e) from about 0.06% to about 0.09% of potassium chloride (% w/v),
(f) from about 0.03% to about 0.06% of calcium chloride (% w/v),
(g) from about 0.01% to about 0.05% of magnesium chloride (% w/v),
(h) from about 0.30% to about 0.50% of sodium acetate (% w/v),
(i) from about 0.10% to about 0.25% of sodium citrate (% w/v)
(j) water for injection, and
(k) optionally, a pH adjusting agent.

In one aspect, the present disclosure provides triamcinolone acetonide suspensions consisting essentially of:
(a) from about 0.35 to about 0.45 mg/mL of triamcinolone acetonide,
(b) from about 0.50% to about 0.60% of sodium chloride (% w/v),
(c) from about 0.4% to about 0.6% of carboxymethylcellulose sodium (% w/v),
(d) from about 0.01% to about 0.03% of polysorbate 80 (% w/v),
(e) from about 0.06% to about 0.09% of potassium chloride (% w/v),
(f) from about 0.03% to about 0.06% of calcium chloride (% w/v),
(g) from about 0.01% to about 0.05% of magnesium chloride (% w/v),
(h) from about 0.30% to about 0.50% of sodium acetate (% w/v),
(i) from about 0.10% to about 0.25% of sodium citrate (% w/v)
(j) water for injection, and
(k) optionally, a pH adjusting agent, wherein the degree of flocculation of the suspension is from about 15 to about 20.

The present disclosure also provides a method of preparing a triamcinolone acetonide suspension comprising the steps of:
(a) heating one or more wetting agents, one or more tonicity agents, one or more pH buffer agents, and triamcinolone acetonide particles;
(b) cooling the suspension of Step (a);
(c) adding an aqueous solution of one or more viscosity agents to the suspension of Step (b);
(d) stirring the suspension of Step (c) at a low-shear stirring rate; and
(e) sonicating the suspension of Step (d),
wherein the suspension comprises about 40 mg/mL of triamcinolone acetonide.

The present disclosure also provides triamcinolone acetonide suspensions that are prepared according to the methods disclosed herein.

In one aspect, the present disclosure provides a packaged product comprising a triamcinolone acetonide suspension as disclosed herein in a suitable container.

The present disclosure provides a kit comprising: (a) a triamcinolone acetonide suspension as disclosed herein in a suitable container and (b) a suspension delivery system for suprachoroidal injection of the suspension. In some embodiments, the suspension delivery system comprises a syringe and at least one microneedle. In some embodiments, the diameter of the microneedle is about 30 gauge and the length of the microneedle is selected from 900 μm and 1100 μm.

The present disclosure also provides methods of treating ocular disorders in a patient in need thereof by administering an effective amount of a triamcinolone acetonide suspension of the present disclosure to the posterior region of the patient's eye by suprachoroidal injection.

DETAILED DESCRIPTION OF THE DRAWINGS

DETAILED DESCRIPTION OF THE DISCLOSURE

Definitions

Figure 1:
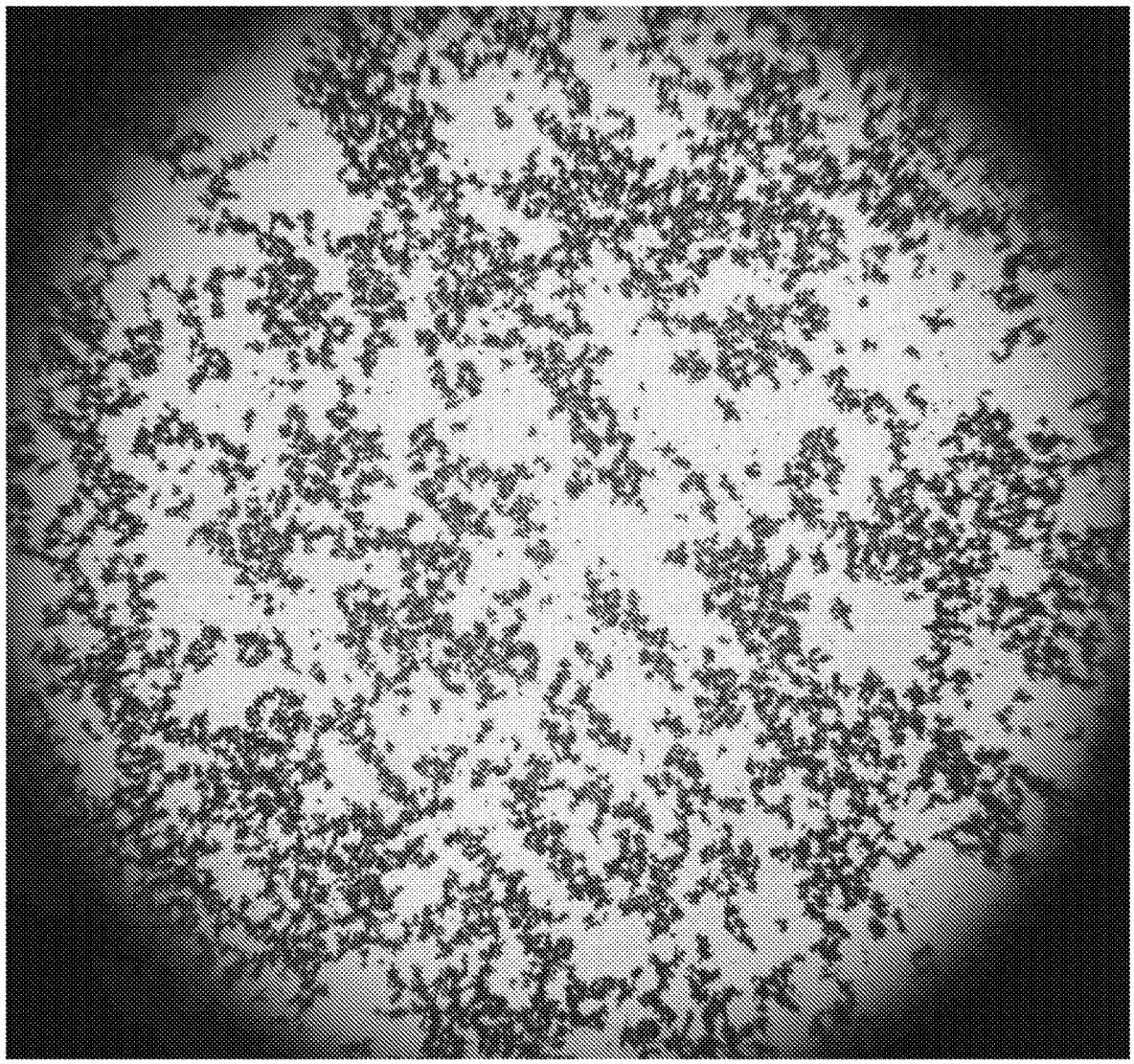
FIG. 1 shows the microscopic analysis of a dispersed triamcinolone acetonide suspension that is essentially free of aggregates.

Throughout this disclosure, various patents, patent applications and publications are referenced. The disclosures of these patents, patent applications and publications in their entireties are incorporated into this disclosure by reference for all purposes in order to more fully describe the state of the art as known to those skilled therein as of the date of this disclosure. This disclosure will govern in the instance that there is any inconsistency between the patents, patent applications and publications cited and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

The term "about" when immediately preceding a numerical value means a range (e.g., plus or minus 10% of that value). For example, "about 50" can mean 45 to 55, "about 25,000" can mean 22,500 to 27,500, etc., unless the context of the disclosure indicates otherwise, or is inconsistent with such an interpretation. For example in a list of numerical values such as "about 49, about 50, about 55, . . . ", "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein. Similarly, the term "about" when preceding a series of numerical values or a range of values (e.g., "about 10, 20, 30" or "about 10-30") refers, respectively to all values in the series, or the endpoints of the range.

"Administering" includes any mode of administration. "Administering" can also include prescribing or filling a prescription for a dosage form comprising a particular compound. "Administering" can also include providing directions to carry out a method involving a particular compound or a dosage form comprising the compound. In some embodiments, "administering" includes suprachoroidal injection by the methods described in U.S. Publication Nos. US 2015/0258120, US 2010/0256597, and US2018/0042765, each of which is hereby incorporated by reference in its entirety for all purposes. In some embodiments, "administering" includes suprachoroidal injection using a device described in U.S. Publication No. US 2017/0112665, which is hereby incorporated by reference in its entirety for all purposes.

The term "suprachoroidal space," is used interchangeably with suprachoroidal, SCS, suprachoroid and suprachoroidia, and describes the potential space in the region of the eye disposed between the sclera and choroid. This region primarily is composed of closely packed layers of long pigmented processes derived from each of the two adjacent tissues; however, a space can develop in this region as a result of fluid or other material buildup in the suprachoroidal space and the adjacent tissues. The term "supraciliary space," as used herein, is encompassed by the SCS and refers to the most anterior portion of the SCS adjacent to the ciliary body, trabecular meshwork and limbus. Those skilled in the art will appreciate that the suprachoroidal space frequently is expanded by fluid buildup because of some disease state in the eye or as a result of some trauma or surgical intervention. In the present description, however, the fluid buildup is intentionally created by infusion of a drug formulation into the suprachoroid to create the suprachoroidal space (which is filled with drug formulation). Not wishing to be bound by theory, it is believed that the SCS region serves as a pathway for uveoscleral outflow (i.e., a natural process of the eye moving fluid from one region of the eye to the other through) and becomes a real space in instances of choroidal detachment from the sclera.

"Degree of flocculation" means the ratio of the final sediment volume (i.e., as a percentage of the total volume) to particle concentration. For example, a suspension with a 2% particle concentration and a final sediment volume of 30% would have a Degree of flocculation of 15. Similarly, a suspension with a 2% particle concentration and a final sediment volume of 40% would have a Degree of flocculation of 20.

"Glide force" means the force required to maintain plunger movement once static friction has been overcome. As used herein "glide force" is measured between 1 and 7 seconds, when the syringe piston is in motion.

"Syringeability Force Test" means the syringe force test described in Example 3. In some embodiments, the Syringeability Force Test is used to determine whether a suspension of the present disclosure is syringeable (e.g., that the suspension is essentially free of TA aggregates that cause flow resistance and prevent syringeability through a 33 G ½ gauge needle).

The terms "effective amount" and "therapeutically effective amount" are used interchangeably in this disclosure and refer to an amount of a compound, or a salt, solvate or ester thereof, that, when administered to a patient, is capable of performing the intended result. For example, an effective amount of triamcinolone acetonide suspension is that amount that is required to reduce at least one symptom of an ocular disease (such as macular edema associated with non-infectious uveitis, retinal vein occlusion and diabetic macular edema) in a patient. The actual amount that comprises the "effective amount" or "therapeutically effective amount" will vary depending on a number of conditions including, but not limited to, the severity of the disorder, the size and health of the patient, and the route of administration. A skilled medical practitioner can readily determine the appropriate amount using methods known in the medical arts.

Triamcinolone Acetonide Suspensions, Packaged Products and Kits

The present disclosure provides triamcinolone acetonide suspensions that are stable, readily resuspendable/redispersible, essentially particulate-free and suitable for administration via suprachoroidal injection.

In some embodiments, the triamcinolone acetonide suspensions of the present disclosure are characterized on the basis of their physical properties (e.g., being essentially particulate- and aggregate-free, degree of flocculation, viscosity, average glide force required to deliver the suspension through a microneedle, syringeability, particle size distribution) that make them suited for packaging with consistent triamcinolone acetonide weights and assays in each container and for administration via intraocular injection.

In some embodiments, the present disclosure provides essentially particulate-free and aggregate-free pharmaceutical suspensions of triamcinolone acetonide. In such embodiments, the pharmaceutical suspensions of triamcinolone acetonide are essentially free of visible (e.g., particles greater than about 100 μm), foreign particles (i.e., particulate matter that is not related to the triamcinolone acetonide active ingredient) as determined by the methods described herein. Furthermore, in such embodiments, the pharmaceutical suspensions of triamcinolone acetonide are essentially free of aggregated particles of triamcinolone acetonide (or aggregate-free) as determined by the methods described herein.

Figure 2:
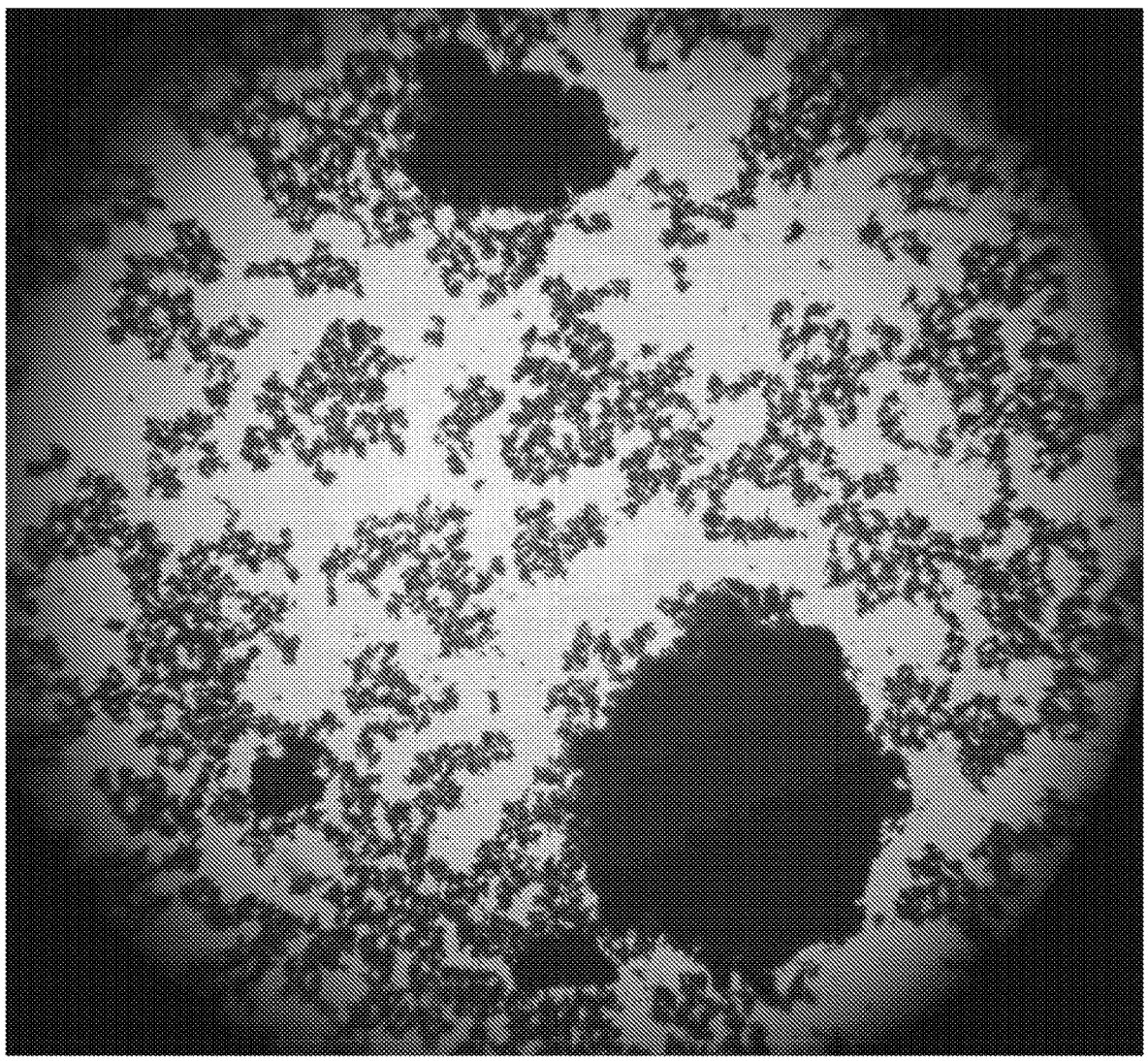
FIG. 2 shows the microscopic analysis of a dispersed triamcinolone acetonide suspension that contains aggregates.
Figure 3:
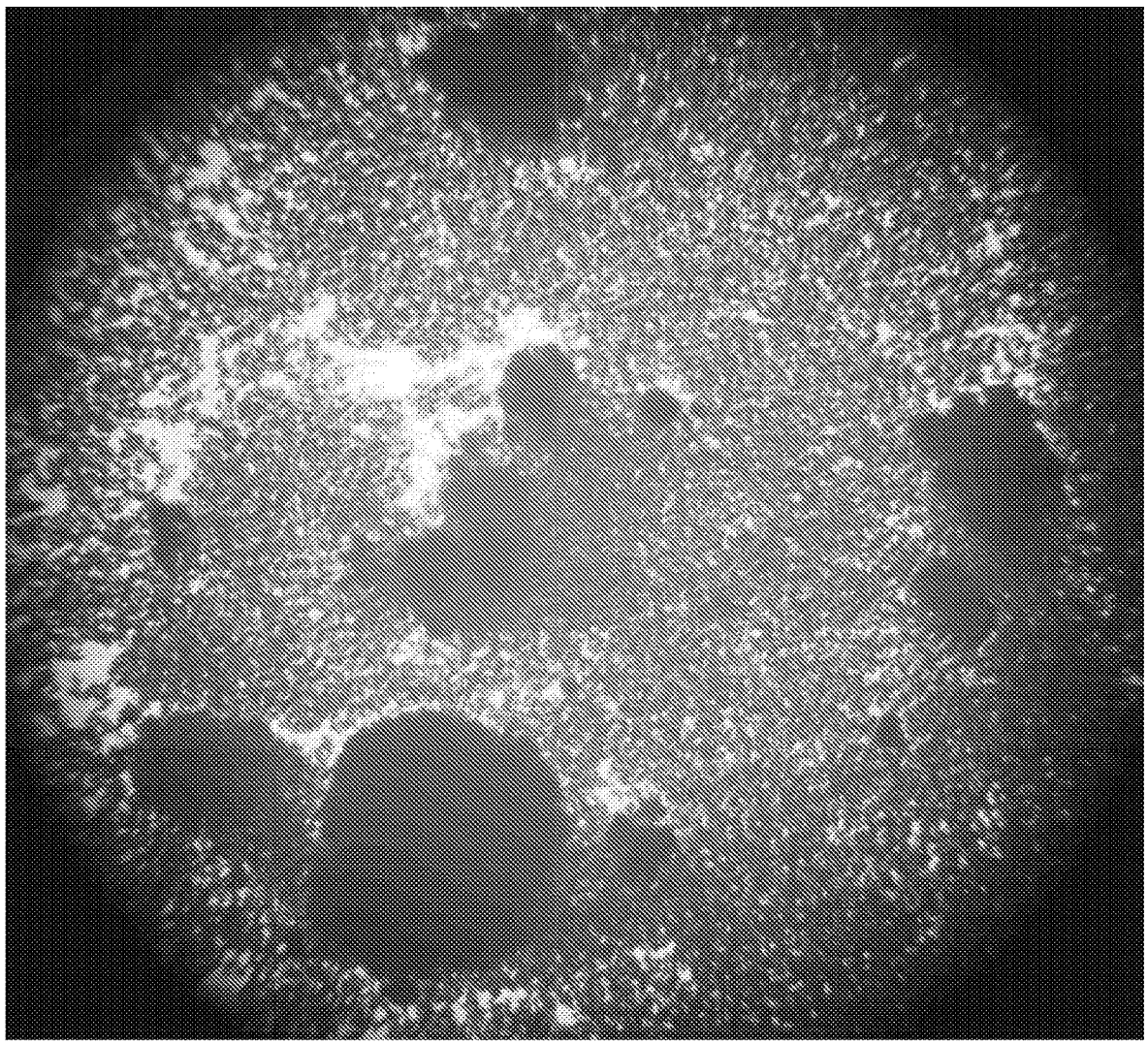
FIG. 3 shows the microscopic analysis of a dense triamcinolone acetonide suspension that contains aggregates.

For reference, FIG. 1 shows the microscopic analysis of a dispersed triamcinolone acetonide suspension that is essentially free of aggregates; FIG. 2 shows the microscopic analysis of a dispersed triamcinolone acetonide suspension that contains aggregates; and FIG. 3 shows the microscopic analysis of a dense triamcinolone acetonide suspension that contains aggregates.

In some embodiments, the triamcinolone acetonide suspensions of the present disclosure are essentially particulate- and aggregate-free, as determined by any suitable method known in the art.

In some embodiments, the triamcinolone acetonide suspensions of the present disclosure are essentially aggregate-free as determined by a Syringeability Force Test described in Example 3 (i.e., the suspension is essentially free of TA aggregates that cause flow resistance and reduce syringeability). In some embodiments, triamcinolone acetonide suspensions of the present disclosure are essentially aggregate-free as characterized by a Syringeability Force Distribution ($D_f 90$) of the suspension that is not more than about 780 $g^f$, not more than about 760 $g^f$, not more than about 740 $g^f$, not more than about 720 $g^f$, not more than about 700 $g^f$, not more than about 680 $g^f$, not more than about 660 $g^f$ or not more than 640 $g^f$ as determined by the Syringeability Force Test. In some embodiments, the triamcinolone acetonide suspensions of the present disclosure are essentially aggregate-free as characterized by a Syringeability Force Distribution ($D_f 90$) of the suspension that is not more than about 760 $g^f$ as determined by the Syringeability Force Test described in Example 3.

In some embodiments, the triamcinolone acetonide suspensions of the present disclosure are described on the basis of their syringeability (i.e., the ability of the suspension to be passed through a fine-gauge needle without plugging). In some embodiments, the present disclosure provides suspensions containing about 40 mg/mL of triamcinolone acetonide, wherein about 100 μL of the triamcinolone acetonide suspension dispenses through a 30 gauge needle without plugging. In other embodiments, the present disclosure provides suspensions containing about 40 mg/mL of triamcinolone acetonide, wherein about 300 μL of the triamcinolone acetonide suspension dispenses through a 33 gauge needle without plugging.

In some embodiments, the triamcinolone acetonide suspensions of the present disclosure are essentially particulate-free as determined by the USP<790> test method or the USP<1790> test method. In some embodiments, the triamcinolone acetonide suspensions of the present disclosure are essentially particulate-free as determined by microscopy and/or a light obscuration (such as, USP<788> Method 1 Light Obscuration Particle Count Test), to evaluate the presence of particulate matter in the suspension.

In some embodiments, the triamcinolone acetonide suspensions of the present disclosure are described on the basis of the particle size of the triamcinolone acetonide in the suspension. In some embodiments, the triamcinolone acetonide suspensions of the present disclosure are essentially free of triamcinolone acetonide particles having a particle size greater than about 150 μm, greater than about 200 μm, greater than about 250 μm, greater than about 300 μm, greater than about 350 μm, greater than about 400 μm, greater than about 450 μm or greater than about 500 μm.

In some embodiments, the triamcinolone acetonide particles have a $D_{10}$ of less than about 3.0 μm, less than about 2.5 μm, less than about 2.0 μm, less than about 1.5 μm, less than about 1.0 μm, or less than about 0.5 μm. In some embodiments, the triamcinolone acetonide particles have a $D_{10}$ of less than about 1.0 μm.

In some embodiments, the triamcinolone acetonide particles have a $D_{50}$ of less than about 7.0 μm, less than about 6.0 μm, less than about 5.0 μm, less than about 4.0 μm, or less than about 3.0 μm. In some embodiments, the triamcinolone acetonide particles have a $D_{50}$ of less than about 5.0 μm.

In some embodiments, the triamcinolone acetonide particles have a $D_{90}$ of less than about 12.0 μm, less than about 11.0 μm, less than about 10.0 μm, less than about 9.0 μm, less than about 8.0 μm, less than about 7.0 μm, or less than about 5.0 μm. In some embodiments, the triamcinolone acetonide particles have a $D_{90}$ of less than about 10.0 μm.

In some embodiments, the triamcinolone acetonide suspensions of the present disclosure are characterized on the basis of the average floc size (i.e., average particle size) of the triamcinolone acetonide in the suspension. In some embodiments, the triamcinolone acetonide suspensions are characterized by having an average floc size (i.e., average particle size) of the triamcinolone acetonide in the suspension of from about 80 μm to about 120 μm, including about 85 μm, about 90 μm, about 95 μm, about 100 μm, about 105

µm, and about 115 µm, including all ranges there between. In some embodiments, the triamcinolone acetonide suspensions are characterized by having an average floc size (i.e., average particle size) of the triamcinolone acetonide in the suspension is from about 90 µm to about 110 µm.

In some embodiments, the triamcinolone acetonide suspensions are characterized by having an average floc size (i.e., average particle size) of the triamcinolone acetonide in the suspension of about 80 µm, 85 µm, about 90 µm, about 95 µm, about 100 µm, about 105 µm, about 115 µm, or about 120 µm. In some embodiments, the triamcinolone acetonide suspensions are characterized by having an average floc size (i.e., average particle size) of the triamcinolone acetonide in the suspension of about 100 µm.

In some embodiments, the triamcinolone acetonide suspensions of the present disclosure are characterized on the basis of their degree of flocculation. In some embodiments, the triamcinolone acetonide suspensions are characterized by having a degree of flocculation from about 15 to about 20, including about 16, about 17, about 18, and about 19, including all ranges there between. In some embodiments, the triamcinolone acetonide suspensions are characterized by having a degree of flocculation of about 15, about 16, about 17, about 18, about 19 or about 20. In some embodiments, the triamcinolone acetonide suspensions are characterized by having a degree of flocculation of about 17. In some embodiments, the triamcinolone acetonide suspensions are characterized by having a degree of flocculation of at least about 15, at least about 16, at least about 17, at least about 18, at least about 19 or at least about 20. In some embodiments, the triamcinolone acetonide suspensions are characterized by having a degree of flocculation of at least about 15. In some embodiments, the triamcinolone acetonide suspensions are characterized by having a degree of flocculation of at least about 17.

In some embodiments, an essentially particulate- and aggregate-free pharmaceutical suspension is characterized by having essentially no particulates or aggregates greater than about 50 µm, greater than about 45 µm, greater than about 40 µm, greater than about 35 µm, greater than about 30 µm, greater than about 25 µm, greater than about 20 µm, greater than about 15 µm, greater than about 10 µm, or greater than about 5 µm. In some embodiments, an essentially particulate- and aggregate-free pharmaceutical suspension is characterized by having essentially no particulates or aggregates about 50 µm or greater in size. In some embodiments, an essentially particulate- and aggregate-free pharmaceutical suspension is characterized by having essentially no particulates or aggregates about 40 µm or greater in size. In some embodiments, an essentially particulate- and aggregate-free pharmaceutical suspension is characterized by having essentially no particulates or aggregates about 30 µm or greater in size. In some embodiments, an essentially particulate- and aggregate-free pharmaceutical suspension is characterized by having essentially no particulates or aggregates about 20 µm or greater in size. In some embodiments, an essentially particulate- and aggregate-free pharmaceutical suspension is characterized by having essentially no particulates or aggregates about 10 µm or greater in size. In some embodiments, an essentially particulate- and aggregate-free pharmaceutical suspension is characterized by having essentially no particulates or aggregates about 5 µm or greater in size.

In some embodiments, the present disclosure provides essentially particulate-free and aggregate-free pharmaceutical suspensions of triamcinolone acetonide. In some embodiments, the pharmaceutical suspensions are particle- and aggregate-free as determined by any suitable test method known in the art. In some embodiments, the test method for evaluating visible particulate matter in a suspension of the present disclosure is the USP<790> test method or the USP<1790> test method (version USP 42-NF 37). In some embodiments, a light obscuration or microscopy method is used in addition to the aforementioned methods to evaluate the presence of visible particulate matter in the suspensions of the present disclosure.

In some embodiments, the triamcinolone acetonide suspensions of the present disclosure are described on the basis of their redispersibility (i.e., the ability of a stored suspension to provide a uniform suspension that is free of aggregates when vigorously agitated). In some embodiments, the present disclosure provides suspensions containing about 40 mg/mL of triamcinolone acetonide, wherein after 10 seconds of vigorous agitation, microscopic analysis of the agitated suspension indicates a homogenous suspension that is visually dispersed and is free of aggregates.

In some embodiments, the triamcinolone acetonide suspensions of the present disclosure are characterized on the basis of their viscosity. In some embodiments, the triamcinolone acetonide suspensions are characterized by having viscosity of from about 5 cPs to about 20 cPs, including about 6 cPs, about 7 cPs, about 8 cPs, about 9 cPs, about 10 cPs, about 11 cPs, about 12 cPs, about 13 cPs, about 14 cPs, about 15 cPs, about 16 cPs, about 17 cPs, about 18 cPs and about 19 cPs, including all ranges there between. In some embodiments, the triamcinolone acetonide suspensions are characterized by having viscosity of from about 8 cPs to about 12 cPs. In some embodiments, the triamcinolone acetonide suspensions are characterized by having a viscosity of about 5 cPs, about 6 cPs, about 7 cPs, about 8 cPs, about 9 cPs, about 10 cPs, about 11 cPs about 12 cPs, about 13 cPs, about 14 cPs, about 15 cPs, about 16 cPs, about 17 cPs, about 18 cPs, about 19 cPs, or about 20 cPs. In some embodiments, the triamcinolone acetonide suspensions are characterized by having a viscosity of about 10 cPs.

In some embodiments, the triamcinolone acetonide suspensions of the present disclosure are characterized on the basis of their settling times. In some embodiments, the triamcinolone acetonide suspensions are characterized by having the following settling times:

| Time (hr) | Sedimentation (%) |
| --- | --- |
| 0 | 102.0 |
| 1 | 91.8 |
| 2 | 81.6 |
| 3 | 68.4 |
| 4 | 68.4 |
| 6 | 68.4 |
| 7 | 68.4 |
| 8 | 68.4 |

As used herein, the "settling time" is determined by the following procedure (referred to herein as the "Settling Test"):

(a) Re-disperse the triamcinolone acetonide suspension to prepare a homogenous suspension. Redispersion may be achieved by vigorously shaking a suspension-containing bottle or by mixing the suspension using an external mixer.

(b) Transfer approximately 10 mL of dispersed triamcinolone acetonide suspension into a 10 mL graduated cylinder.

(c) Record the height of the triamcinolone acetonide suspension (mL) in the graduated cylinder at the initial reading.
(d) Monitor the suspension about every hour for up to about 8 hours, or until suspension settles.
(e) Record the results in a table as shown below; record the data in mL of suspension and then convert to percentage based up on the initial reading.

| Time | Suspension height ("SH") (mL) | Sedimentation (%) |
|---|---|---|
| T = 0 hr | | $(SH_{T=0}/SH_{T=0}) \times 100$ |
| T = 1 hr | | $(SH_{T=1}/SH_{T=0}) \times 100$ |
| T = 2 hr | | $(SH_{T=2}/SH_{T=0}) \times 100$ |
| T = 3 hr | | $(SH_{T=3}/SH_{T=0}) \times 100$ |
| T = 4 hr | | $(SH_{T=4}/SH_{T=0}) \times 100$ |
| T = 5 hr | | $(SH_{T=5}/SH_{T=0}) \times 100$ |
| T = 6 hr | | $(SH_{T=6}/SH_{T=0}) \times 100$ |
| T = 7 hr | | $(SH_{T=7}/SH_{T=0}) \times 100$ |
| T = 8 hr | | $(SH_{T=8}/SH_{T=0}) \times 100$ |

In some embodiments, the disclosure provides triamcinolone acetonide suspensions comprising about 40 mg/mL of triamcinolone acetonide, and a wetting agent, wherein the composition is essentially particulate-free and aggregate-free.

In some embodiments, the pharmaceutical suspension of the present disclosure comprises about 40 mg/mL of triamcinolone acetonide; and a wetting agent; wherein the injection of the suspension through a 30-gauge needle of 900 μm to 1100 μm length provides an average glide force of less than about 1.00 Newton. In some embodiments, the compositions comprise at least about 0.02% w/v of the wetting agent. In some embodiments, the wetting agent is polysorbate 80.

In some embodiments, the injection of the suspensions of the present disclosure through a 30 gauge needle of 1100 μm length provides an average glide force of less than about 1.20 N, including less than about 1.15 N, less than about 1.10 N, less than about 1.05 N, less than about 1.00 N, less than about 0.90 N, less than about 0.85 N, less than about 0.80 N, less than about 0.75 N, less than about 0.70 N, less than about 0.65 N, less than about 0.60 N, less than about 0.55 N, less than about 0.50 N, less than about 0.45 N and less than about 0.40 N. In some embodiments, the injection of the suspensions of the present disclosure through a 30 gauge needle of 1100 μm length provides an average glide force of about 1.20 N, including about 1.15 N, about 1.10 N, about 1.05 N, about 1.00 N, about 0.90 N, about 0.85 N, about 0.80 N, about 0.75 N, about 0.70 N, about 0.65 N, about 0.60 N, about 0.55 N, about 0.50 N, about 0.45 N and about 0.40 N. In some embodiments, the injection of the suspension through a 30-gauge needle of 900 μm to 1100 μm length provides an average glide force of less than about 0.9 N, about 0.8 N or about 0.7 N.

In some embodiments, the present disclosure provides suspensions containing about 40 mg/mL of triamcinolone acetonide, wherein the average floc size (i.e., average particle size) of the triamcinolone acetonide is from about 80 μm to about 120 μm, and a wetting agent wherein the injection of the suspension through a 30-gauge needle of 900 μm to 1100 μm length provides an average glide force of less than about 1.00 Newton (N). In some embodiments, the present disclosure provides suspensions containing about 40 mg/mL of triamcinolone acetonide, wherein the average floc size (i.e., average particle size) of the triamcinolone acetonide is about 100 μm, and a wetting agent wherein the injection of the suspension through a 30-gauge needle of 900 μm to 1100 μm length provides an average glide force of less than about 1.00 Newton (N). In some embodiments, the compositions comprise at least about 0.02% w/v of the wetting agent. In some embodiments, the wetting agent is polysorbate 80. In some embodiments, the injection of the suspensions of the present disclosure through a 30 gauge needle of 900 μm to 1100 μm length provides an average glide force of less than about 1.20 N, including less than about 1.15 N, less than about 1.10 N, less than about 1.05 N, less than about 1.00 N, less than about 0.90 N, less than about 0.85 N, less than about 0.80 N, less than about 0.75 N, less than about 0.70 N, less than about 0.65 N, less than about 0.60 N, less than about 0.55 N, less than about 0.50 N, less than about 0.45 N and less than about 0.40 N. In some embodiments, the injection of the suspensions of the present disclosure through a 30 gauge needle of 900 μm to 1100 μm length provides an average glide force of about 1.20 N, including about 1.15 N, about 1.10 N, about 1.05 N, about 1.00 N, about 0.90 N, about 0.85 N, about 0.80 N, about 0.75 N, about 0.70 N, about 0.65 N, about 0.60 N, about 0.55 N, about 0.50 N, about 0.45 N and about 0.40 N.

The triamcinolone acetonide suspensions of the present disclosure are characterized on the basis of their composition.

In some embodiments, the triamcinolone acetonide suspensions of the present disclosure comprise about 5 mg/mL, about 8 mg/mL, about 10 mg/mL, about 20 mg/mL, about 25 mg/mL, about 30 mg/mL, about 35 mg/mL, about 40 mg/mL, about 45 mg/mL, about 50 mg/mL, about 55 mg/mL about 60 mg/mL, about 65 mg/mL, about 70 mg/mL, about 75 mg/mL, or about 80 mg/mL of triamcinolone acetonide and one or more pharmaceutically acceptable excipient. In some embodiments, the triamcinolone acetonide suspensions of the present disclosure comprise about 40 mg/mL of triamcinolone acetonide and one or more pharmaceutically acceptable excipients.

In some embodiments, the triamcinolone acetonide suspensions of the present disclosure comprise at least about 15 mg/mL, at least about 20 mg/mL, at least about 25 mg/mL, at least about 30 mg/mL, at least about 35 mg/mL, at least about 40 mg/mL, at least about 45 mg/mL, at least about 50 mg/mL, or at least about 55 mg/mL of triamcinolone acetonide and one or more pharmaceutically acceptable excipients. In some embodiments, the triamcinolone acetonide suspensions of the present disclosure comprise at least about 35 mg/mL of triamcinolone acetonide and one or more pharmaceutically acceptable excipients.

Pharmaceutical excipients suitable for administration by suprachoroidal injection are known to those skilled in the art include, for example, isotonicity agents, viscosity agents, wetting agents, pH buffers and solvent.

In some embodiments, the triamcinolone acetonide suspensions comprise an isotonicity agent. In some embodiments, the isotonicity agent is selected from the group consisting of betadex sulfobutyl ether sodium, calcium chloride, dextrose, dimethyl-β-cyclodextrin, glycerin, hydroxyethyl-β-cyclodextrin, hydroxypropyl betadex, magnesium chloride, magnesium oxide, maltodextrin, mannitol, potassium chloride, sodium chloride and trimethyl-β-cyclodextrin. In some embodiments, the isotonicity agent is selected from the group consisting of sodium chloride, potassium chloride, calcium chloride and magnesium chloride.

In some embodiments, the triamcinolone acetonide suspensions comprise a viscosity agent. In some embodiments, the viscosity agent is selected from the group consisting of acacia, agar, alginic acid, aluminum monostearate, ammonium sulfate, attapulgite, bentonite, betadex sulfobutyl ether sodium, calcium alginate, calcium lactate, carbomers, carboxymethylcellulose calcium, carboxymethylcellulose sodium with microcrystalline cellulose, carrageenan, cellulose microcrystalline, carboxymethylcellulose sodium, ceratonia, ceresin, cetostearyl alcohol, cetyl palmitate, chitosan, colloidal silicon dioxide, corn syrup solids, cyclomethicone, dextrin, ethylcellulose, gelatin, gellan gum, glycerin, glyceryl behenate, glyceryl laurate, guar gum, hectorite, hydrogenated palm oil, hydrogenated vegetable oil type I, hydrophobic colloidal silica, hydroxyethyl cellulose, hydroxyethylmethyl cellulose, hydroxypropyl cellulose, hypromellose, magnesium aluminum silicate, maltodextrin, methylcellulose, microcrystalline cellulose, and carboxymethylcellulose sodium, modified starch, myristyl alcohol, octyldodecanol, pectin, polycarbophil, polydextrose, polyethylene glycol, polyethylene oxide, poly(methylvinyl ether/maleic anhydride), polyoxyethylene alkyl ethers, polyvinyl alcohol, potassium alginate, povidone, propylene glycol alginate, propylene glycol dilaurate, pullulan, saponite, sodium alginate, sodium chloride, starch, stearic acid, stearyl alcohol, sucrose, tragacanth, trehalose, and xanthan gum. In some embodiments, the viscosity agent is carboxymethylcellulose sodium.

In some embodiments, the triamcinolone acetonide suspensions comprise a wetting agent. In some embodiments, the wetting agent is selected from the group consisting of alcohol (such as ethanol), glyceryl monooleate, benzethonium chloride, docusate sodium, emulsifying wax BP, hypromellose, phospholipids, polyethylene alkyl ethers, sodium lauryl sulfate, tricaprylin, benzalkonium chloride, cetrimide, cetrimonium bromide, cetylpyridinium chloride, xanthan gum, alpha tocopherol, butylparaben, ethylparaben, methylparaben, potassium sorbate, propylparaben, sorbic acid, emulsifying wax USP, glyceryl laurate, myristyl alcohol, poloxamer, polyoxyethylene alkyl ethers, polyoxyethylene castor oil derivatives, polyoxyethylene sorbitan fattyacid esters, polyoxyethylene stearates, polyoxyl 15 hydroxystearate, polyoxylglycerides, polysorbate 80, propylene glycol dilaurate, propylene glycol monolaurate, sorbitan esters, sucrose palmitate, sucrose stearate, tyloxapol, vitamin E polyethylene glycol succinate. In some embodiments, the wetting agent is tyloxapol. In some embodiments, the wetting agent is polysorbate 80.

In some embodiments, the triamcinolone acetonide suspensions comprise a pH buffer agent. In some embodiments, the pH buffer agent is selected from the group consisting of acetic acid, adipic acid, ammonia solution, ammonium phosphate, ammonium sulfate, arginine, asparagine, boric acid, calcium carbonate, calcium lactate, tribasic calcium phosphate, citric acid monohydrate, dibasic potassium phosphate, dibasic sodium phosphate, diethanolamine, glycine, histidine, hydroxyethylpiperazine ethanesulfonic acid, lysine acetate, lysine hydrochloride, maleic acid, malic acid, meglumine, methionine, monobasic sodium phosphate, monoethanolamine, monosodium glutamate, phosphoric acid, potassium citrate, potassium metaphosphate, sodium acetate, sodium bicarbonate, sodium borate, sodium carbonate, sodium citrate, sodium lactate, triethanolamine, and tromethamine. In some embodiments, the pH buffer agent comprises sodium acetate and sodium citrate.

In some embodiments, the triamcinolone acetonide suspensions comprise pH adjusting agent. In some embodiments, the pH adjusting agent is selected from the group consisting of sodium hydroxide, hydrochloric acid, aqueous ammonia, diethanolamine, meglumine, sodium citrate, acetic acid, adipic acid, ammonium chloride, ascorbic acid, citric acid, fumaric acid, gluconolactone, lactic acid, maleic acid, malic acid, monobasic sodium phosphate, phosphoric acid, propionic acid, sulfuric acid, tartaric acid, calcium hydroxide, monoethanolamine, potassium bicarbonate, potassium citrate, potassium hydroxide, sodium bicarbonate, sodium borate, sodium carbonate, sodium citrate, triethanolamine, and tromethamine. In some embodiments, the pH adjusting agent comprises sodium hydroxide and hydrochloric acid.

In some embodiments, the triamcinolone acetonide suspensions of the present disclosure are characterized using a combination of their composition and physical properties.

In some embodiments, the triamcinolone acetonide suspensions consist essentially of:
 (a) from about 0.35 to about 0.45 mg/mL of triamcinolone acetonide, wherein the average floc size (i.e., average particle size) of the triamcinolone acetonide is about 80 μm to about 120 μm,
 (b) from about 0.4% to about 0.6% of one or more viscosity agents (% w/v),
 (c) from about 0.01% to about 0.03% of one or more wetting agents (% w/v),
 (d) from about 0.6% about to about 0.8% of one or more tonicity agents (% w/v),
 (e) from about 0.5% to about 0.7% of one or more pH buffer agents (% w/v),
 (f) water for injection, and
 (g) optionally, a pH adjusting agent.

In some embodiments, the triamcinolone acetonide suspensions consist essentially of:
 (a) from about 0.35 to about 0.45 mg/mL of triamcinolone acetonide, wherein the average floc size (i.e., average particle size) of the triamcinolone acetonide is about 80 μm to about 120 μm,
 (b) from about 0.50% to about 0.60% of sodium chloride (% w/v),
 (c) from about 0.4% to about 0.6% of carboxymethylcellulose sodium (% w/v),
 (d) from about 0.01% to about 0.03% of polysorbate 80 (% w/v),
 (e) from about 0.06% to about 0.09% of potassium chloride (% w/v),
 (f) from about 0.03% to about 0.06% of calcium chloride (% w/v),
 (g) from about 0.01% to about 0.05% of magnesium chloride (% w/v),
 (h) from about 0.30% to about 0.50% of sodium acetate (% w/v),
 (i) from about 0.10% to about 0.25% of sodium citrate (% w/v),
 (j) water for injection, and
 (k) optionally, a pH adjusting agent.

In some embodiments, the triamcinolone acetonide suspensions consist essentially of:
 (a) from about 40 mg/mL of triamcinolone acetonide, wherein the average floc size (i.e., average particle size) of the triamcinolone acetonide is about 80 μm to about 120 μm,
 (b) about 0.5% of carboxymethylcellulose sodium (% w/v),
 (c) about 0.02% of polysorbate 80 (% w/v),
 (d) about 0.7% of one or more tonicity agents (% w/v),
 (e) about 0.6% of one or more buffer agents (% w/v),
 (f) water for injection, and
 (g) optionally, a pH adjusting agent.

In some embodiments, the triamcinolone acetonide suspensions consist essentially of:
(a) from about 0.40 mg/mL of triamcinolone acetonide, wherein the average floc size (i.e., average particle size) of the triamcinolone acetonide is from about 80 µm to about 120 µm,
(b) about 0.55% sodium chloride (% w/v),
(c) about 0.5% carboxymethylcellulose sodium (% w/v),
(d) about 0.02% polysorbate 80 (% w/v),
(e) about 0.075%, potassium chloride (% w/v),
(f) about 0.048% calcium chloride (% w/v),
(g) about 0.03% magnesium chloride (% w/v),
(h) about 0.39% sodium acetate (% w/v),
(i) about 0.17% sodium citrate (% w/v),
(j) water for injection, and
(k) optionally, a pH adjusting agent.

In some embodiments, the triamcinolone acetonide suspensions consist essentially of:
(a) from about 0.35 to about 0.45 mg/mL of triamcinolone acetonide,
(b) from about 0.4% to about 0.6% of one or more viscosity agents (% w/v),
(c) from about 0.01% to about 0.03% of one or more wetting agents (% w/v),
(d) from about 0.6% about to about 0.8% of one or more tonicity agents (% w/v),
(e) from about 0.5% to about 0.7% of one or more pH buffer agents (% w/v),
(f) water for injection, and
(g) optionally, a pH adjusting agent, wherein the degree of flocculation of the suspension is from about 15 to about 20.

In some embodiments, the triamcinolone acetonide suspensions consist essentially of:
(a) from about 0.35 to about 0.45 mg/mL of triamcinolone acetonide,
(b) from about 0.50% to about 0.60% of sodium chloride (% w/v),
(c) from about 0.4% to about 0.6% of carboxymethylcellulose sodium (% w/v),
(d) from about 0.01% to about 0.03% of polysorbate 80 (% w/v),
(e) from about 0.06% to about 0.09% of potassium chloride (% w/v),
(f) from about 0.03% to about 0.06% of calcium chloride (% w/v),
(g) from about 0.01% to about 0.05% of magnesium chloride (% w/v),
(h) from about 0.30% to about 0.50% of sodium acetate (% w/v),
(i) from about 0.10% to about 0.25% of sodium citrate (% w/v),
(j) water for injection, and
(k) optionally, a pH adjusting agent, wherein the degree of flocculation of the suspension is from about 15 to about 20.

In some embodiments, the triamcinolone acetonide suspensions consist essentially of:
(a) about 40 mg/mL of triamcinolone acetonide,
(b) about 0.5% of carboxymethylcellulose sodium (% w/v),
(c) about 0.02% of polysorbate 80 (% w/v),
(d) about 0.7% of one or more tonicity agents (% w/v),
(e) about 0.6% of one or more buffer agents (% w/v),
(f) water for injection, and
(g) optionally, a pH adjusting agent, wherein the degree of flocculation of the suspension is from about 15 to about 20.

In some embodiments, the triamcinolone acetonide suspensions consist essentially of:
(a) about 0.40 mg/mL of triamcinolone acetonide,
(b) about 0.55% sodium chloride (% w/v),
(c) about 0.5% carboxymethylcellulose sodium (% w/v),
(d) about 0.02% polysorbate 80 (% w/v),
(e) about 0.075%, potassium chloride (% w/v),
(f) about 0.048% calcium chloride (% w/v),
(g) about 0.03% magnesium chloride (% w/v),
(h) about 0.39% sodium acetate (% w/v),
(i) about 0.17% sodium citrate (% w/v),
(j) water for injection, and
(k) optionally, a pH adjusting agent, wherein the degree of flocculation of the suspension is from about 15 to about 20.

In one aspect, the present disclosure provides a packaged product comprising a triamcinolone acetonide suspension of the present disclosure in a suitable container. Suitable containers for suspensions that are ocularly administered are known to those skilled in the art and include, without limitation, glass vial and blow, fill and seal containers. In some embodiments, the suitable container is a glass vial. In some embodiments, the glass vial contains from about 0.5 mL, about 0.6 mL, about 0.7 mL, about 0.8 mL, about 0.9 mL, about 1.0 mL, about 1.1 mL, about 1.2 mL, about 1.3 mL, about 1.4 mL or about 1.5 mL of the suspension of the present disclosure. In some embodiments, the glass vial contains about 0.9 mL of the suspension of the present disclosure. In some embodiments, the glass vial contains from about 0.5 mL to about 1.5 mL, including about 0.6 mL, about 0.7 mL, about 0.8 mL, about 0.9 mL, about 1.0 mL, about 1.1 mL, about 1.2 mL, about 1.3 mL, and about 1.4 mL including all ranges there between of the suspension of the present disclosure.

In one aspect, the present disclosure provides kits comprising the triamcinolone acetonide suspensions of the present disclosure. In some embodiments, the kits of the present disclosure comprise:
(a) a triamcinolone acetonide suspension of the present disclosure in a suitable container and
(b) a suspension delivery system for suprachoroidal injection of the suspension.

In some embodiments, the suitable container is a glass vial. In some embodiments, the glass contains about 0.9 mL of the suspension of the present disclosure.

In some embodiments, the suspension delivery system comprises a syringe and at least one microneedle. In some embodiments, the diameter of the microneedle is about 30 gauge. In some embodiments, the length of the microneedle is selected from 900 µm and 1100 µm.

In some embodiments, the kits of the present disclosure comprise:
(a) about 0.9 mL of a triamcinolone acetonide suspension of the present disclosure in a glass vial,
(b) a vial adaptor, and
(c) a suspension delivery system comprising
(i) a syringe,
(ii) a 30-gauge microneedle of 900 µm length and
(iii) a 30-gauge microneedle of 1100 µm length.

Triamcinolone Acetonide Suspension Processes

The present disclosure provides methods for preparing triamcinolone acetonide suspensions that are stable, readily resuspendable/redispersible and suitable for administration via suprachoroidal injection. In particular, the methods provide triamcinolone acetonide suspensions having a viscosity, degree of flocculation and settling times that are particularly suited to prepare and package commercial quantities of an FDA-approved triamcinolone acetonide suspension drug product.

In some embodiments, the present disclosure provides a process of preparing a pharmaceutical suspension comprising:
(a) providing an essentially particulate-free first solution comprising one or more viscosity agents, one or more one tonicity agents, and one or more pH buffer agents in an aqueous solvent;
(b) providing an essentially particulate-free second solution comprising one or more wetting agents in an aqueous solvent;
(c) adding triamcinolone acetonide particles to the solution of Step (b) to provide a suspension;
(d) adding the suspension of Step (c) to the solution of Step (a); and
(e) sonicating the suspension of Step (d),
wherein the suspension comprises about 40 mg/mL of triamcinolone acetonide In some embodiments of the present disclosure, a pharmaceutical suspension is prepared by a process comprising:
(a) heating one or more wetting agents, one or more tonicity agents, one or more pH buffer agents, and triamcinolone acetonide particles;
(b) cooling the suspension of Step (a);
(c) adding an aqueous solution of one or more viscosity agents to the suspension of Step (b);
(d) stirring the suspension of Step (c) at a low-shear stirring rate; and
(e) sonicating the suspension of Step (d),
to provide a triamcinolone acetonide suspension that is suitable for administration via suprachoroidal injection.

In some embodiments, the triamcinolone acetonide particles used to prepare the suspension have a $D_{50}$ of from about 0.5 µm to about 5.0 µm, including about 1.0 µm, about 1.5 µm, about 2.0 µm, about 2.5 µm, about 3.0 µm, about 3.5 µm, about 4.0 µm and about 4.5 µm, including all ranges and values there between. In some embodiments, the triamcinolone acetonide particles have a $D_{50}$ of from about 2.0 µm to about 3.0 µm. In some embodiments, the triamcinolone acetonide particles have a $D_{50}$ of about 0.5 µm, about 1.0 µm, about 1.5 µm, about 2.0 µm, about 2.5 µm, about 3.0 µm, about 3.5 µm, about 4.0 µm, about 4.5 µm, and about 5.0 µm. In some embodiments, the triamcinolone acetonide particles have a $D_{50}$ of about 2 µm.

In some embodiments, the triamcinolone acetonide particles used to prepare the suspension have a $D_{50}$ of less than about 5.0 µm, less than about 4.5 µm, less than about 4.0 µm, less than about 3.5 µm, less than about 3.0 µm, less than about 2.5 µm, or less than about 2.0 µm. In some embodiments, the triamcinolone acetonide particles have a $D_{50}$ of less than about 5.0 µm. In some embodiments, the triamcinolone acetonide particles have a $D_{50}$ of less than about 3.0 µm. In some embodiments, the triamcinolone acetonide particles have a $D_{50}$ of less than about 2.5 µm.

In some embodiments, the triamcinolone acetonide particles used to prepare the suspension have a $D_{70}$ of from about 0.5 µm to about 5.0 µm, including about 1.0 µm, about 1.5 µm, about 2.0 µm, about 2.5 µm, about 3.0 µm, about 3.5 µm, about 4.0 µm and about 4.5 µm, including all ranges and values there between. In some embodiments, the triamcinolone acetonide particles have a $D_{70}$ of from about 2.0 µm to about 3.0 µm. In some embodiments, the triamcinolone acetonide particles have a $D_{70}$ of about 0.5 µm, about 1.0 µm, about 1.5 µm, about 2.0 µm, about 2.5 µm, about 3.0 µm, about 3.5 µm, about 4.0 µm, about 4.5 µm, and about 5.0 µm. In some embodiments, the triamcinolone acetonide particles have a $D_{70}$ of about 2 µm.

In some embodiments, the triamcinolone acetonide particles used to prepare the suspension have a $D_{70}$ of less than about 5.0 µm, less than about 4.5 µm, less than about 4.0 µm, less than about 3.5 µm, less than about 3.0 µm, less than about 2.5 µm, or less than about 2.0 µm. In some embodiments, the triamcinolone acetonide particles have a $D_{70}$ of less than about 5.0 µm. In some embodiments, the triamcinolone acetonide particles have a $D_{70}$ of less than about 3.0 µm. In some embodiments, the triamcinolone acetonide particles have a $D_{70}$ of less than about 2.5 µm.

In some embodiments, the triamcinolone acetonide particles used to prepare the suspension have a $D_{70}$ of less than about 5.0 µm, less than about 4.5 µm, less than about 4.0 µm, less than about 3.5 µm, less than about 3.0 µm, less than about 2.5 µm, or less than about 2.0 µm and a $D_{99}$ of less than about 10 µm.

In some embodiments, the triamcinolone acetonide particles used to prepare the suspension have a $D_{99}$ of less than about 15 µm, less than about 14 µm, less than about 12 µm, less than about 11 µm, less than about 10 µm, less than about 9 µm, or less than about 8 µm. In some embodiments, the $D_{99}$ is less than about 10 µm.

In some embodiments, the triamcinolone acetonide particles used to prepare the suspension have a $D_{70}$ of less than about 5.0 µm and a $D_{99}$ of less than about 10 µm.

In some embodiments, the one or more wetting agents is selected from the group consisting of alcohol (such as ethanol), glyceryl monooleate, docusate sodium, emulsifying wax BP, hypromellose, phospholipids, polyethylene alkyl ethers, sodium lauryl sulfate, tricaprylin, benzalkonium chloride, benzethonium chloride, cetrimide, cetrimonium bromide, cetylpyridinium chloride, xanthan gum, alpha tocopherol, butylparaben, ethylparaben, methylparaben, potassium sorbate, propylparaben, sorbic acid, emulsifying wax USP, glyceryl laurate, myristyl alcohol, poloxamer, polyoxyethylene alkyl ethers, polyoxyethylene castor oil derivatives, polyoxyethylene sorbitan fatty-acid esters, polyoxyethylene stearates, polyoxyl 15 hydroxystearate, polyoxylglycerides, polysorbate 80, propylene glycol dilaurate, propylene glycol monolaurate, sorbitan esters, sucrose palmitate, sucrose stearate, vitamin E polyethylene glycol succinate. In some embodiments, the one or more wetting agents is polysorbate 80. In some embodiments, the suspension comprises about 0.1% w/v polysorbate 80, about 0.08% w/v polysorbate 80, about 0.06% w/v polysorbate 80, about 0.04% w/v polysorbate 80, or about 0.02% w/v polysorbate 80. In some embodiments, the suspension comprises about 0.02% w/v polysorbate 80.

In some embodiments, the one or more isotonicity agents is selected from the group consisting of betadex sulfobutyl ether sodium, dextrose, dimethyl-β-cyclodextrin, glycerin, hydroxypropyl betadex, hydroxyethyl-β-cyclodextrin, magnesium oxide, maltodextrin, mannitol, trimethyl-β-cyclodextrin, sodium chloride, potassium chloride, calcium chloride and magnesium chloride. In some embodiments, the one or more tonicity agents comprises sodium chloride, potassium chloride, calcium chloride, and magnesium chloride. In some embodiments, the one or more tonicity agents is selected from the group consisting of sodium chloride, potassium chloride, calcium chloride, and magnesium chloride.

In some embodiments, the one or more pH buffer agents is selected from the group consisting of acetic acid, adipic acid, ammonia solution, ammonium phosphate, ammonium sulfate, arginine, asparagine, boric acid, calcium carbonate, calcium lactate, tribasic calcium phosphate, citric acid monohydrate, dibasic potassium phosphate, dibasic sodium phosphate, diethanolamine, glycine, histidine, hydroxyethylpiperazine ethane sulfonic acid, lysine acetate, lysine hydrochloride, maleic acid, malic acid, meglumine, methionine, monobasic sodium phosphate, monoethanolamine, monosodium glutamate, phosphoric acid, potassium citrate, potassium metaphosphate, sodium acetate, sodium bicarbonate, sodium borate, sodium carbonate, sodium citrate, sodium lactate, triethanolamine, tromethamine. In some embodiments, the one or more pH buffer agents is selected from sodium acetate and sodium citrate.

In some embodiments, the one or more viscosity agents is selected from the group consisting of acacia, agar, alginic acid, aluminum monostearate, ammonium sulfate, attapulgite, bentonite, betadex sulfobutyl ether sodium, calcium alginate, calcium lactate, carbomers, carboxymethylcellulose calcium, carboxymethylcellulose sodium with microcrystalline cellulose, carrageenan, cellulose microcrystalline, carboxymethylcellulose sodium, ceratonia, ceresin, cetostearyl alcohol, cetyl palmitate, chitosan, colloidal silicon dioxide, corn syrup solids, cyclomethicone, dextrin, ethylcellulose, gelatin, gellan gum, glycerin, glyceryl behenate, glyceryl laurate, guar gum, hectorite, hydrogenated palm oil, hydrogenated vegetable oil type I, hydrophobic colloidal silica, bydroxyethyl cellulose, hydroxyethylmethyl cellulose, hydroxypropyl cellulose, hypromellose, magnesium aluminum silicate, maltodextrin, methylcellulose, microcrystalline cellulose, and carboxymethylcellulose sodium, modified starch, myristyl alcohol, octyldodecanol, pectin, polycarbophil, polydextrose, polyethylene glycol, polyethylene oxide, poly(methylvinyl ether/maleic anhydride), polyoxyethylene alkyl ethers, polyvinyl alcohol, potassium alginate, povidone, propylene glycol alginate, propylene glycol dilaurate, pullulan, saponite, sodium alginate, sodium chloride, starch, stearic acid, stearyl alcohol, sucrose, tragacanth, trehalose, and xanthan gum. In some embodiments, the one or more viscosity agents is carboxymethylcellulose sodium. In some embodiments, the concentration of carboxymethylcellulose sodium in the aqueous solution is about 9 mg/mL.

In some embodiments, the essentially particulate-free first solution of Step (a) is provided by:
  (a) filtering a solution comprising one or more viscosity agents;
  (b) filtering a solution comprising one or more one tonicity agents, and one or more pH buffer agents in an aqueous solvent; and
  (c) combining the solutions of Step (a) and Step (b) to provide the essentially particulate-free first solution.

In some embodiments, the solutions are filtered through a 0.5 μm pore size filter, a 0.5 μm pore size filter, a 0.3 μm pore size filter, a 0.2 μm pore size filter, or a 0.1 μm pore size filter. In some embodiments, the solutions are filtered through a 0.2 μm pore size filter.

In some embodiments, the essentially particulate-free second solution of Step (b) is provided by filtering a solution comprising one or more wetting agents in an aqueous solvent to provide the essentially particulate-free first solution. In some embodiments, the essentially particulate-free second solution is filtered through a 0.5 μm pore size filter, a 0.5 μm pore size filter, a 0.3 μm pore size filter, a 0.2 μm pore size filter, or a 0.1 μm pore size filter. In some embodiments, the solutions are filtered through a 0.2 μm pore size filter. In some embodiments, the essentially particulate-free second solution is filtered through a 0.2 μm pore size filter.

In some embodiments, combining the solutions of Step (a) and Step (b) is under continuous stirring. In some embodiments, the stirring is maintained at a speed ranging from about 300 rpm to about 500 rpm. In some embodiments, the stirring speed is maintained at a speed ranging from about 330 rpm to about 370 rpm. In some embodiments, the stirring is maintained at about 350 rpm.

In some embodiments, the mixture of one or more wetting agents, one or more tonicity agents, one or more pH buffer agents, and triamcinolone acetonide particles in Step (a) is heated to a temperature and for a time that reduces the bioburden of the suspension but does not adversely affect the physical properties of the suspension. In some embodiments, the mixture of Step (a) is heated to about 120° C. In some embodiments, the mixture of Step (a) is heated to about 120° C. for a time that reduces the bioburden of the suspension but does not adversely affect the physical properties of the suspension. In some embodiments, the mixture of Step (a) is heated to about 120° C. for about 15 minutes.

The Applicants unexpectedly discovered that Step (d) stirring the suspension of Step (c), described above, under conditions that are commonly used in the art (such as about 250 rpm) provided a rapid decrease in suspension viscosity (9 cps to 4 cps) such that the resulting suspensions are not suitable for consistent product packaging and administration via suprachoroidal injection (e.g., the decreased viscosity provides faster settling rates). Without being bound by any theory, it is believed that stirring the viscosity agent (e.g., carboxymethylcellulose sodium) at about 250 rpm degrades the carboxymethylcellulose sodium to smaller components thereby decreasing the suspension viscosity. Applicants discovered that by reducing the stirring speed in Step (d) to a low-shear stirring rate, the viscosity of the suspensions is maintained. In some embodiments, the low-shear stirring rate in Step (d) is a rate that does not substantially decrease the viscosity of the suspension compared to the viscosity prior to said stirring. As understood by those skilled in the art, the stirring rate that provides low-shear will depend on various factors including the size and shape of the stirring vessel, the shape of the stirring tip, etc. In some embodiments, the low-shear stirring rate in Step (d) is less than about 120 rpm. In some embodiments, the low-shear stirring rate in Step (d) is from about 60 rpm to about 120 rpm, including about 70 rpm, about 80 rpm, about 90 rpm, about 100 rpm, about 110 rpm including all ranges there between. In some embodiments, the low-shear stirring rate in Step (d) is less than about 200 rpm. In some embodiments, the low-shear stirring rate in Step (d) is from about 150 rpm to about 200 rpm, including about 160 rpm, about 170 rpm, about 180 rpm, and about 190 rpm, including all ranges there between.

Furthermore, the Applicants discovered that heating suspensions containing of carboxymethylcellulose sodium, which was thought to be required to reduce the bioburden of the suspension, substantially decreased suspension viscosity, degree of flocculation and settling times. Applicants discovered that filtering aqueous solutions of carboxymethylcellulose sodium through certain polyether sulfone filter membranes provided bioburden reduction without reducing the viscosity of the suspensions that contain the carboxymethylcellulose sodium. In some embodiments, prior to Step (c) adding an aqueous solution of one or more viscosity agents to the suspension of Step (b), an aqueous solution containing carboxymethylcellulose sodium is filtered through a membrane having a laid over pleat shape. In some embodiments, prior to Step (c), an aqueous solution containing carboxymethylcellulose sodium is filtered through a polyether sulfone filter membrane. In some embodiments, prior to Step (c), an aqueous solution containing carboxymethylcellulose sodium is filtered through a polyether sulfone filter membrane having a laid over pleat shape. In some embodiments, the polyether sulfone filter membrane is Supor EX grade ECV. In some embodiments, the pore size of the polyether sulfone filter membrane is about 0.22 µm.

In some embodiments, the method further comprises adjusting the pH of the suspension of Step (d). In some embodiments, adjusting the pH comprises the addition of acid. In some embodiments, adjusting the pH comprises the addition of about 1% hydrochloric acid by total batch weight. In some embodiments, the pH is adjusted to a value of about 6-7. In some embodiments, the pH is adjusted to a value of about 6.4-6.7.

In some embodiments, the sonication of Step (e) is conducted until the suspension is essentially aggregate-free. In some embodiments, the sonication of Step (e) is conducted until the suspension is essentially aggregate-free as determined by a Syringeability Force Test. In some embodiments, the sonication of Step (e) is conducted until the Syringeability Force Distribution ($D_f90$) of the suspension is not more than about 760 $g_f$.

Syringeability force, as used herein, measures the force required to dispense a pharmaceutical suspension of the present disclosure from a syringe through a microneedle. In some embodiments, the syringeability force is the force required to dispense 0.3 mL of a suspension through a 33 gauge ½ inch needle at a rate of about 0.014 mL/second to about 0.016 mL/second. In some embodiments, the dispensing occurs over about 19 seconds to about 21 seconds. In some embodiments, only data from the 3rd second to the 16th second is recorded to ensure break force (initial force to move the syringe) and end of dispensing readings are not included.

In some embodiments, the method further comprises filtering the sonication suspension of Step (e). In some embodiments, the suspension of Step (e) is filtered through a 50-250 µm pore size filter. In some embodiments, the suspension of Step (e) is filtered through a 50-100 µm pore size filter. In some embodiments, the suspension of Step (e) is filtered through a 100-250 µm pore size filter. In some embodiments, the suspension of Step (e) is filtered through a 234 µm pore size filter. In some embodiments, the suspension of Step (e) is filtered through a 200 µm pore size filter. In some embodiments, the suspension of Step (e) is filtered through a 150 µm pore size filter. In some embodiments, the suspension of Step (e) is filtered through a 100 µm pore size filter. In some embodiments, the suspension of Step (e) is filtered through a 50 µm pore size filter.

In some embodiments, the sonication in Step (e) is conducted such that, after the sonication, the triamcinolone acetonide suspension is characterized by having a degree of flocculation from about 15 to about 20, including about 16, about 17, about 18, and about 19, including all ranges there between. In some embodiments, the sonication in Step (e) is conducted such that, after the sonication, the triamcinolone acetonide suspension is characterized by having a degree of flocculation of about 15, about 16, about 17, about 18, about 19 or about 20. In some embodiments, the sonication in Step (e) is conducted such that, after the sonication, the triamcinolone acetonide suspension is characterized by having a degree of flocculation of about 17. In some embodiments, the sonication in Step (e) is conducted such that, after the sonication, the triamcinolone acetonide suspensions suspension is by having a degree of flocculation of at least about 15, at least about 16, at least about 17, at least about 18, at least about 19 or at least about 20. In some embodiments, the sonication in Step (e) is conducted such that, after the sonication, the triamcinolone acetonide suspension is characterized by having a degree of flocculation of at least about 17.

In some embodiments, the sonication in Step (e) is conducted such that, after the sonication, the triamcinolone acetonide suspension is characterized by having the following settling times:

| Time (hr) | Sedimentation (%) |
|---|---|
| 0 | 102.0 |
| 1 | 91.8 |
| 2 | 81.6 |
| 3 | 68.4 |
| 4 | 68.4 |
| 6 | 68.4 |
| 7 | 68.4 |
| 8 | 68.4 |

In some embodiments, the sonication in Step (e) is conducted such that, after the sonication, the average floc size (i.e., average particle size) of the triamcinolone acetonide is from about 80 µm to about 120 µm, including about 85 µm, about 90 µm, about 95 µm, about 100 µm, about 105 µm, and about 115 µm, including all ranges there between. In some embodiments, the sonication in Step (e) is conducted such that, after the sonication, the average floc size (i.e., average particle size) of the triamcinolone acetonide in the suspension is from about 90 µm to about 110 µm.

In some embodiments, the sonication in Step (e) is conducted such that, after the sonication, the average floc size (i.e., average particle size) of the triamcinolone acetonide in the suspension is about 80 µm, 85 µm, about 90 µm, about 95 µm, about 100 µm, about 105 µm, about 115 µm, or about 120. In some embodiments, the triamcinolone acetonide suspensions are characterized by having an average floc size (i.e., average particle size) of the triamcinolone acetonide in the suspension of about 100 µm.

In some embodiments, the sonication in Step (e) comprises sonicating the suspension of Step (d) using an ultrasonic probe. In some embodiments, the ultrasonic probe is set to an energy of about 762 W.s during the sonication. In some embodiments, the sonication in Step (e) is conducted for about 12 minutes to about 20 minutes. In some embodiments, the sonication in Step (e) is conducted for about 12 minutes to about 20 minutes using an ultrasonic probe set to an energy of about 762 W.s. In some embodiments, the sonication in Step (e) is repeated at least one time, at least two times, at least three times, at least four times or at least five times.

In some embodiments, the process of the present disclosure further comprises sterilizing the sonicated suspension of Step (e). Suitable sterilization methods are known to those skilled in the art and include, without limitation, autoclaving and radiation.

Figure 5:
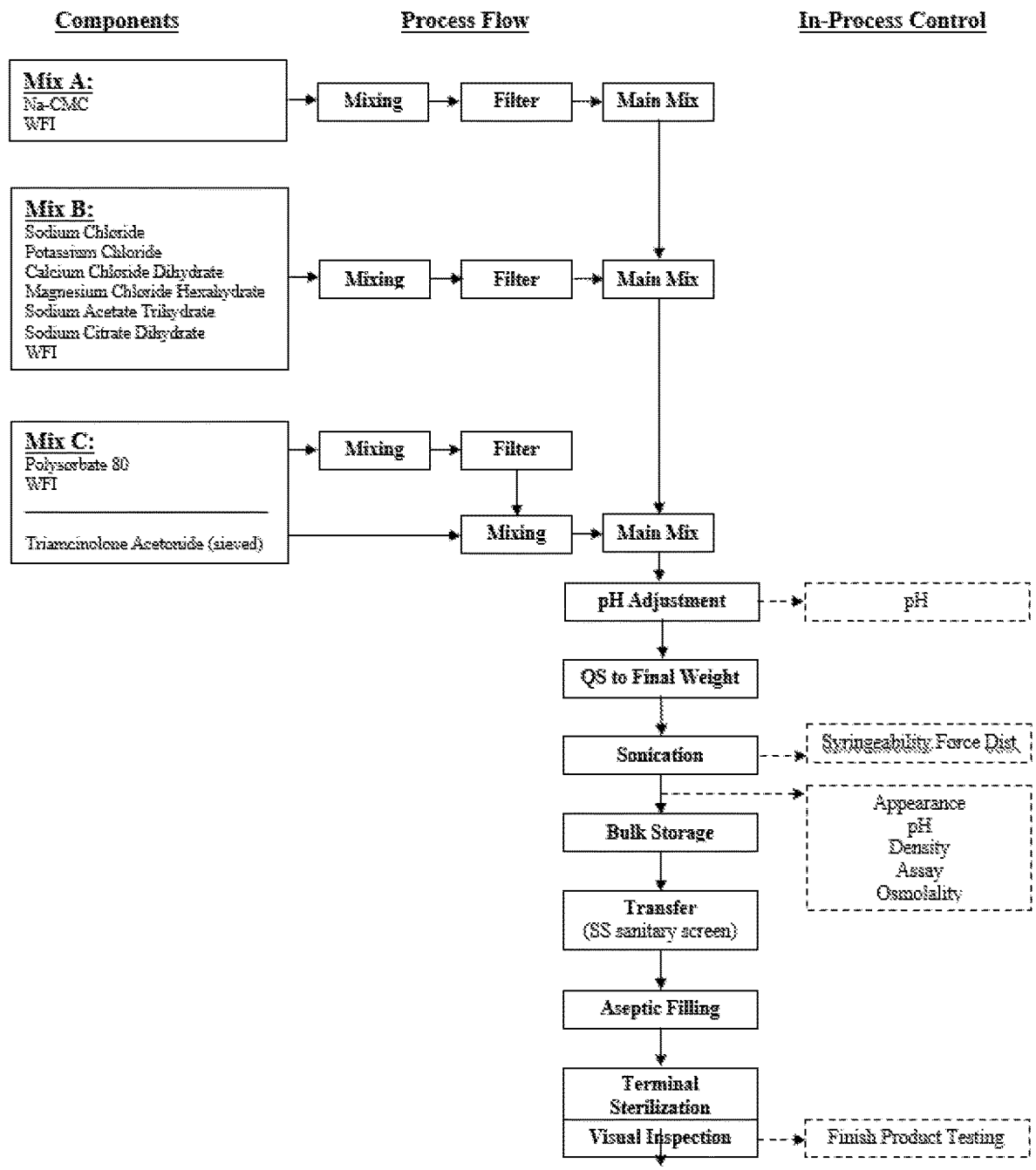
FIG. 5 shows flow diagram that describes a process for preparing an essentially particulate- and aggregate-free pharmaceutical suspension according to the present disclosure.

In some embodiments, the process of preparing an essentially particulate- and aggregate-free pharmaceutical suspension is carried out according to the steps disclosed in FIG. 5. In some embodiments, the process disclosed in FIG. 5 is carried out according to the process parameters listed in Table 2.

In some embodiments, the process of the present disclosure further comprises filling the suspension of Step (e) into a suitable container. In some embodiments, the suitable container is sterile. In some embodiments, the container is a glass vial. In some embodiments, about 0.9 mL of the suspension is packaged in a 2 mL glass vial. In some embodiments, the glass vial is filled using a piston drive or peristaltic pump system. In some embodiments, the filling provides a consistent weight of triamcinolone acetonide as indicated by providing packaged triamcinolone acetonide suspensions having a content uniformity that meets the requirements of the USP <905> Uniformity of Dosage Units test. In some embodiments, the filling provides a consistent assay of triamcinolone acetonide as indicated by providing packaged triamcinolone acetonide suspensions having an assay of about 90.0% to about 110.0% (by weight) of the product label claim as determined by high performance liquid chromatography.

In some embodiments, the methods of the present disclosure provide packaged triamcinolone acetonide suspensions having a content uniformity that meet FDA requirements for suspension drug products. In some embodiments, the methods of the present disclosure provide packaged triamcinolone acetonide suspensions having a content uniformity that meets the requirements of the USP <905> Uniformity of Dosage Units test. In other embodiments, the methods of the present disclosure provide packaged triamcinolone acetonide suspensions having an assay of about 90.0% to about 110.0% (by weight) of the product label claim as determined by high performance liquid chromatography. In some embodiments, the methods of the present disclosure provide packaged triamcinolone acetonide suspensions having an assay of about 36.0 mg/mL to about 44.0 mg/mL for a product claiming a concentration of 40 mg/mL as determined by high performance liquid chromatography.

The present invention also provides the triamcinolone acetonide suspensions prepared according to the processes set forth above.

Methods of Using Triamcinolone Acetonide Suspensions

The present disclosure also provides methods of treating treatment of posterior ocular disorders, choroidal maladies and other diseases associated with vascular abnormalities in a patient by administering an effective amount of a suspension of the present disclosure to the posterior region of the patient's eye.

Devices and methods of using such devices suitable for delivering the suspensions of the present disclosure into the posterior region of the patient's eye (such as the suprachoroidal space of the eye) are described in U.S. Publication No. US 2015/0258120.

Examples of posterior ocular disorders amenable for treatment by the methods and suspensions disclosed herein include, but are not limited to, uveitis, glaucoma, macular edema, diabetic macular edema, macular edema associated with retinal vein occlusion (RVO), macular edema associated with uveitis, retinopathy, diabetic retinopathy, age-related macular degeneration (for example, wet AMD or dry AMD), scleritis, optic nerve degeneration, geographic atrophy, choroidal disease, ocular sarcoidosis, optic neuritis, choroidal neovascularization, autoimmune diseases affecting the posterior segment of the eye, retinitis, and corneal ulcers. The posterior ocular disorders amenable for treatment by the methods and suspensions disclosed herein may be acute or chronic.

In some embodiments, the present disclosure provides a method of treating macular edema in a patient in need thereof comprising administering a therapeutically effective amount of the suspension of the present disclosure to the posterior region of the patient's eye. In some embodiments, the suspension of the present disclosure is administered to the posterior region of the patient's eye by suprachoroidal injection. In some embodiments, the method of treating macular edema comprises administering about 0.1 mL of a suspension of the present disclosure containing about 40 mg/mL of triamcinolone acetonide to the posterior region of the patient's eye by suprachoroidal injection.

In some embodiments, the present disclosure provides a method of treating macular edema associated with retinal vein occlusion in a patient in need thereof comprising administering a therapeutically effective amount of the suspension of the present disclosure to the posterior region of the patient's eye. In some embodiments, the method of treating macular edema associated with retinal vein occlusion comprises administering about 0.1 mL of a suspension of the present disclosure containing about 40 mg/mL of triamcinolone acetonide to the posterior region of the patient's eye by suprachoroidal injection.

In some embodiments, the present disclosure provides a method of treating macular edema associated with non-infectious uveitis in a patient in need thereof comprising administering a therapeutically effective amount of the suspension of the present disclosure to the posterior region of the patient's eye. In some embodiments, the method of treating macular edema associated with non-infectious uveitis comprises administering about 0.1 mL of a suspension of the present disclosure containing about 40 mg/mL of triamcinolone acetonide to the posterior region of the patient's eye by suprachoroidal injection.

In some embodiments, the present disclosure provides a method of treating diabetic macular edema in a patient in need thereof comprising administering a therapeutically effective amount of the suspension of the present disclosure to the posterior region of the patient's eye. In some embodiments, the method of treating diabetic macular edema comprises administering about 0.1 mL of a suspension of the present disclosure containing about 40 mg/mL of triamcinolone acetonide to the posterior region of the patient's eye by suprachoroidal injection.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as acknowledgment or any form of suggestion that they constitute valid prior art or form part of the common general knowledge in any country in the world.

EXAMPLES

The following examples are offered to illustrate but not to limit the compounds and methods disclosed herein. Various modifications may be made by the skilled person without departing from the true spirit and scope of the subject matter disclosed herein.

Example 1: Preparation of Essentially Particulate- and Aggregate-Free Triamcinolone Acetonide Suspension A Triamcinolone Acetonide Suspension of the present disclosure was prepared as described below and in FIG. 5.

A non-limiting composition of the Triamcinolone Acetonide (TA) Suspension is provided in the Table 1.

TABLE 1

Composition of TA Suspension in an Embodiment of the Present Disclosure

| Ingredient | (% w/v or as noted)/mL |
|---|---|
| Triamcinolone acetonide | 40 mg |
| Sodium chloride | 0.55% |
| Carboxymethylcellulose sodium | 0.5% |
| Polysorbate 80 | 0.02% |
| Potassium chloride | 0.075% |
| Calcium chloride dihydrate | 0.048% |
| Magnesium chloride hexahydrate | 0.03% |
| Sodium acetate trihydrate | 0.39% |
| Sodium citrate dihydrate | 0.17% |
| Sodium hydroxide and hydrochloric acid | pH to 5.5-7.5 range |
| Water for Injection | Q.S. to 1 mL |

Preparation of Sodium Carboxymethylcellulose (NaCMC) Solution (Main Mix A):

The Main Mix A was prepared by slowly adding NaCMC to Water for Injection (WFI; about 40% of total batch weight) and mixing the resulting solution until NaCMC was fully dissolved. After complete dissolution, mixing was continued. The NaCMC solution was then filtered through a Sartoguard PES MidiCap1.2/2.0 μm Size 8 filter to prevent particulates.

Preparation of Salt Solution (Mix B):

The Salt Solution was prepared by consecutively adding under continuous stirring Potassium Chloride, Sodium Acetate Trihydrate, Sodium Citrate Dihydrate, Calcium Chloride Dihydrate and Magnesium Chloride Hexahydrate to a vessel with WFI (about 8% of total batch weight). After addition of the first salt, the mixture was stirred until the substance was fully dissolved. Upon complete dissolution, the next salt was added, and the process was repeated with each of the remaining salts. The salt solution was then filtered through a 0.2 μm filter to prevent particulates.

Preparation of Triamcinolone Acetonide (TA) Slurry (Mix C):

Polysorbate 80 was dispensed into a mixing vessel and WFI (about 1% of total batch weight) was added. The mixture was stirred and an additional charge of WFI was added (about 7% of total batch weight). The Tween 80 solution was then filtered through a 0.2 μm filter to prevent particulates. Sieved Triamcinolone Acetonide was slowly added to the mixing vessel and the resulting slurry was mixed until a homogenous dispersion was achieved. Mixing was continued until ready for Step 5.

Preparation of Main Mix for Further Processing

Mix B (Salt Solution) was gradually added to the Main Mix A under continuous stirring. Mix C (TA Slurry) was then slowly added to the Main Mix A under continuous stirring. A small amount of Hydrochloric Acid (HCl), about 1% of total batch weight) was added to the Main Mix A to adjust pH and an in-process control test for pH was performed (Table 2). WFI was added until the target batch weight was reached, and the resulting suspension was further mixed until a homogenous dispersion was achieved. The vessel with the bulk suspension was placed in a sonication bath and sonicated under continuous stirring. Sample was withdrawn from Top, Middle and Bottom of the vessel and analyzed using syringeability force distribution to determine the end point of sonication. Samples were taken for retain and In-Process Control (IPC) testing purposes (Table 3). The bulk suspension was stored at 15-25° C. and protected from light.

Figure 4A:
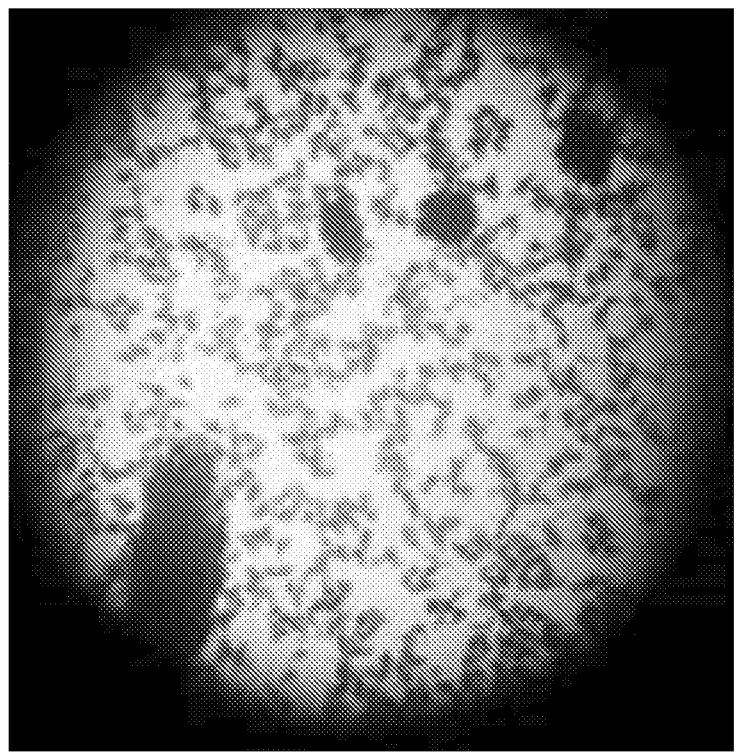
FIG. 4A shows the microscopic analysis of a triamcinolone acetonide suspension of the present disclosure before sonication.
Figure 4B:
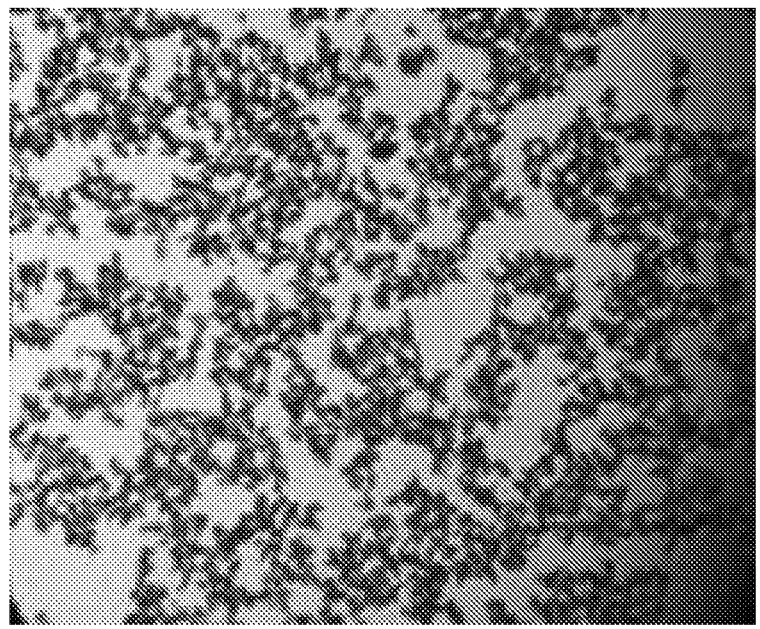
FIG. 4B shows the microscopic analysis of a triamcinolone acetonide suspension of the present disclosure after sonication.

FIG. 4A shows the microscopic analysis of the suspension before sonication. FIG. 4B shows the microscopic analysis of the suspension after sonication. FIG. 4A and FIG. 4B demonstrate that the sonication effectively breaks down aggregates to provide a suspension that is essentially aggregate-free.

A summary of the process parameters for implementing the above process is provided in Table 2.

TABLE 2

Process Parameters for the TA Process of Example 1 (see FIG. 5)

| Process Step | Process Parameters | Target | Range Low | Range High |
|---|---|---|---|---|
| 1 | NaCMC Mixing | Confirm dissolution | | |
| 2 | Salt Mixing | Confirm dissolution | | |
| 3 | Polysorbate 80 Mixing | Confirm dissolution | | |
| | Mixing Speed (TA addition) | 250 RPM (Portion 1) | 230 RPM | 270 RPM |
| | | 375 RPM (Portion 2) | 355 RPM | 395 RPM |
| | | 450 RPM (Portion 3) | 430 RPM | 470 RPM |
| | | 490 RPM (Portion 4) | 470 RPM | 510 RPM |
| | Mixing Time (TA addition) | NLT 15 mins per portion | | |
| | Mixing Speed (TA Slurry) | 490 RPM | 470 RPM | 510 RPM |
| | Mixing Time (TA Slurry) | NLT 120 mins | | |
| 4 | Initial Mixing Speed (Main Mix) | 350 RPM | 330 RPM | 370 RPM |
| 5 | Mixing Speed (Main Mix) | 440 RPM (During TA Slurry addition) | 420 RPM | 460 RPM |
| | Mixing Time (Main Mix) | NLT 10 mins (Post TA Slurry addition) | | |
| | Mixing Speed (Post QS) | 440 RPM | 420 RPM | 460 RPM |
| | Mixing Time (Post QS) | 12.5 mins | 10 mins | 15 mins |
| 8 | Sonication Bath setting | 8 | | |
| | Sonication Time | 16 mins | | |
| | Mixing Speed (Post Sonication) | 450 RPM | 430 RPM | 470 RPM |
| | Mixing Time (Post Sonication) | NLT 10 mins | | |

TABLE 2-continued

Process Parameters for the TA Process of Example 1 (see FIG. 5)

| Process Step | Process Parameters | Target | Range Low | Range High |
|---|---|---|---|---|
| 11 | Sterilization Temperature | ≥122.2° C. | | |
| | Sterilization Time (Exposure) | ≥25 mins | | |
| | Cycle Time | Liquid | | |
| | Cycle Number | 7 | | |

TABLE 3

In-Process Controls (IPC) for the Manufacturing Process Conducted According to Example 1 (see FIG. 5)

| IPC | Process Step | Test | Acceptance Criteria |
|---|---|---|---|
| IPC-1 | 6 | pH | 6.4-6.7 |
| IPC-2 | 8 | Syringeability Force Distribution ($D_f$) | $D_f$90 NMT 760 gf |
| IPC-3 | 9 | Physical Appearance | White to off-white suspension |
| | | pH | 6.0-6.8 |
| | | Osmolality | 270-330 mOsm/kg |
| | | Density | 0.967-1.069 g/ml |
| | | Assay | 38-42 mg/ml |
| | | Bioburden | TAMC: NMT5 CFU/10 mL |
| | | | TYMC: NMT 5CFU/10 mL |
| IPC-4 | 11 | Fill check | 0.825-1.008 g/vial |
| | | Visual Inspection | 100% inspection for visible particulate and defects |

Example 2: Method for Determining Visible Particulate Matter in TA Injectable Suspension The TA injectable suspensions of the present disclosure were determined to be essentially particulate-free in accordance with USP General Chapter<790> and other methods.

Overview: The procedure used in the analysis is based on a modified approach to USP <790> and is applicable to the visible particulate matter determination in the TA injectable suspension. Since the drug product is a suspension, destructive sample preparation was carried out using an ethanol:water system to dissolve the suspension prior to visual inspection. Light obscuration was utilized for verification of the solvent and glassware utilized in this procedure. Once the solvent and glassware were verified to be clean by light obscuration, visible particulate matter was determined according to USP <790>.

Materials and Equipment: Use apparatus and methodology principles are described in USP<788> Method 1 Light Obscuration Particle Count Test and USP<790> Visible Particulate Injections. The following equipment and conditions were used in the present study:

HIAC Liquid Particle Counting System, Model 9703 or equivalent

Pharmspec software, version 3.0 or equivalent

Viewing station, equipped with a Cool-White selection (Fluorescent Bulb) (for visible particles) consisting of an appropriate light source capable of maintaining illumination intensity between 2000 lux and 3750 lux Calibrated light meter capable of reading at least 0-10,000 lux, Fisher Scientific 06-662-64

Particulate-free environment

Powder-free gloves

Calibrated timer 50 mL graduated cylinder or equivalent

Automatic pipet capable of delivering 5 mL of solvent or equivalent.

0.45 μm or finer filter (ethanol compatible)

Glass lined stir bar

Glass vial with septum capable of containing NLT 30 mL of solution that is free of visible scratch marks or defects Reagents used for the analysis are provided in Table 4. Equivalent reagents may be used unless otherwise specified.

TABLE 4

Reagents Specification for Analysis

| Reagent Name | CAS Number | Required Grade, Purity, or Concentration | Suggested Source/Catalog Number |
|---|---|---|---|
| Particle Free Water | NA | Milli-Q or equivalent | In-house |
| Isopropanol | 67-63-0 | Reagent Grade or equivalent | Honeywell |
| Ethanol (200 proof) | 64-17-5 | HPLC or equivalent | Honeywell |
| 70% IPA Presaturated Synthetic Non-shedding Wipers | IPA 67-63-0 DI Water 7732-18-5 | Class 1-1000 | VWR/TWTX1039 (ITW Texwipe ® TX ® 1039 AlphSat ®) |
| Detergent (Micro-90) | NA | NA | VWR/21830-416 |

The following equipment configuration and conditions were used in the particulate matter determination of the TA injectable suspension (Table 5).

TABLE 5

Equipment Configurations and Analysis Conditions

| Instrument Parameters | Parameters Value |
|---|---|
| Number of Runs | 5 |
| Flow Rate | 30 mL/min (HRLD-400) or equivalent |
| Discard First Run | No |
| Stir Rate Setting | 5 (approximately 175 rpm) |
| Tare Volume | 1.00 mL |
| Muitistroke Tare Volume | 0.00 mL |
| Sample Volume | 5.00 mL |

TABLE 5-continued

Equipment Configurations and Analysis Conditions

| Instrument Parameters | Parameters Value |
|---|---|
| Minimum Analysis Channel (≥X μm) | 10 μm, 25 μm, 50 μm, 100 μm, 200 μm |

Equipment and Preparation of Glassware:

The test equipment was maintained in a laminar flow hood or equivalent low-particulate environment.

Glassware and any other equipment was cleaned by immersing and scrubbing in warm, detergent solution.

Glass was rinsed with flowing tap water followed by a rinse of purified water. Flush the HIAC Liquid Particle Counting System with the following reagents in the following sequence: purified water, detergent solution, purified water, IPA, and finally purified water.

Glassware was optionally rinsed with IPA followed by purified water as needed. Glassware was also sonicated with the solvent if steps above were not effective.

Solvent Preparation (50:50 Ethanol/Purified Water):

A suitable volume reservoir was cleaned for preparing the solvent cleaned per the procedure outlined in Section 8.

500 mL of sub-micron filtered water was added to 500 mL of ethanol, mixed thoroughly and filtered through a 0.45 μm or finer ethanol compatible filter (volumes may be appropriately scaled to suit the needs of analysis).

Solvent and Container Verification

Approximately 50 mL of solvent was added to a cleaned, appropriately sized vessel containing a glass lined stir bar utilizing a clean 50 mL graduated cylinder.

Solvent was stirred at 175 rpm for a minimum of two minutes.

The HIAC was flushed with approximately 10 mL of sample solution.

The particulate matter was determined in five sample draws of solvent, each of 5 mL.

Acceptance Criteria: Particles of 10 μm or greater size must be ≤25 for the combined 25 mL. Particles of 50 μm or greater size must be NMT 0 for the combined 25 mL (note: when the acceptance criterion was not met, the solvent was re-filtered if necessary. The glassware was re-cleaned, and the solvent verification test repeated until the results meet the specified acceptance criteria).

Determination of Particles (or Particulates)

A water or methanol dampened wipe was used to remove any residue from the sample vial and the vial was allowed to dry.

At the viewing station, equipped with a fluorescent light source, the sample vial was held by its top, gently swirled, and inverted, while ensuring that no air bubbles were introduced. The sample was observed for about five seconds in front of the Munsell Sheets of color Matte Finish Cat. White # N9. The evaluation process was repeated in front of the Munsell Sheets of color Matte Finish Cat. Black # N2.

When no particles were observed, the suspension was reported as "essentially free from visible particulates." If particles were detected, particle size (large or small) and number were recorded. Large particles were further characterized as spherical, fibrous, or rod-like.

Example 3: Syringeability Force Test Method

The Syringeability Force Test described herein is used to determine whether a suspension is syringeable (e.g., that the suspension is essentially free of TA aggregates that cause flow resistance and prevent syringeability from a 33 G ½ gauge needle). In some embodiments, the Syringeability Force Test is used to determine the end point of sonication in the processes of the present disclosure (such as the sonication step in Example 1).

The objective was to determine the syringeability, or the amount of force required to dispense particulate- and aggregate-free triamcinolone acetonide injectable suspension in-process and bulk drug product from a syringe.

Equipment: (1) analytical balance precise to 0.1 mg or equivalent, (2) TA.XT Plus Texture Analyzer, Stable Micro Systems, (3) Syringe, 1 mL, Leur-Lok, BD, Ref #309628, or equivalent, (4) Disposable needle, 18G×1", Becton Dickinson, or equivalent, (5) Disposable needles, 33G×13 mm, ½", TSK SteriJect Hypodermic, Ref # PRE-33013-100 or equivalent, (6) Rotating Mixer or equivalent sample mixer.

Analyzer settings are provided in Table 6.

TABLE 6

Analyzer Settings

| Parameter | Value |
|---|---|
| Test Mode | Compression |
| Pre-Test Speed | 0.85 mm/sec |
| Test Speed | 0.85 mm/sec |
| Post-Test Speed | 10 mm/sec |
| Target Mode | Force |
| Force | 4029.0 g |
| Trigger Type | Auto(Force) |
| Trigger Force | 20.4 g |
| Break Mode | Off |
| Stop Plot At | Target Position |
| Tare Mode | Auto |
| Advanced Options | On |
| Control Oven | Disabled |
| Wait for Temperature | No |
| Frame Deflection Correction | Off (XT2 compatibility) |
| Points per Second | 10 |

Procedure:

For the purified water, it was ensured that no bubbles were present in the container.

For placebo and product samples, samples were placed on a rotating mixer or similar device and mixed for not less than 10 minutes before sampling. The sample(s) were rotated until all testing was completed for the sample.

About 0.5 mL of sample was withdrawn from the sample container into a 1-mL syringe (an 18 G needle can optionally be used).

The syringe was inverted and sample was expelled until 0.4 mL of the suspension remained in the syringe.

A 33 G ½ inch needle was placed on the syringe.

The syringe was inverted and sample was expelled until 0.3 mL of the suspension remained in the syringe.

The syringe was placed in the texture analyzer assembly and secured by tightening the retaining screws.

Figure 11:
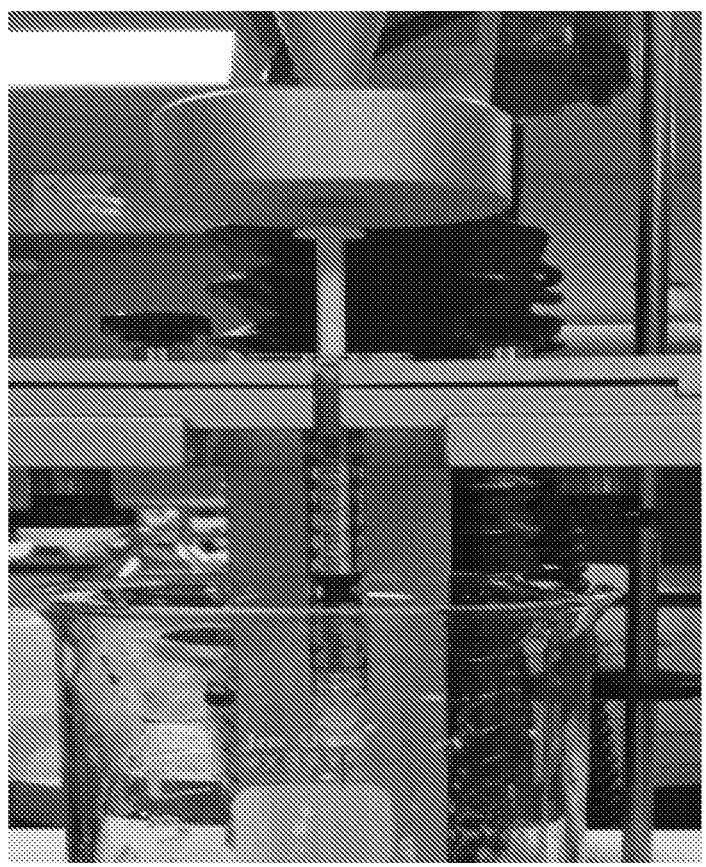
FIG. 11 shows an example syringe set-up for determining syringeability force for an essentially particulate- and aggregate-free TA injectable suspension.

A beaker was set up as shown in FIG. 11.

Fifteen individual tests for performed for each sample, or in the case of in-process testing, five individual tests were performed for the top, middle, and bottom samples of the suspension.

The texture analyzer was run according to the parameters in Table 6.

Sample Analysis

For each sample, fifteen individual were performed, or in the case of in-process testing, five individual tests were performed for each location (top, middle and bottom samples from a single lot) for a total of fifteen tests for the lot.

For each test, a syringe was filled and loaded with suspension as described above in the Procedure section.

The force tester was run according to the parameters in Table 6 and the individual force results were determined from 3 to 16 seconds (a total of 130 data points for each test).

To ensure system suitability, it was confirmed that the baseline between 3-16 seconds was stable.

It was also confirmed that the maximum measured force did not exceed 500 $g^f$.

Data Reporting

Figure 6:
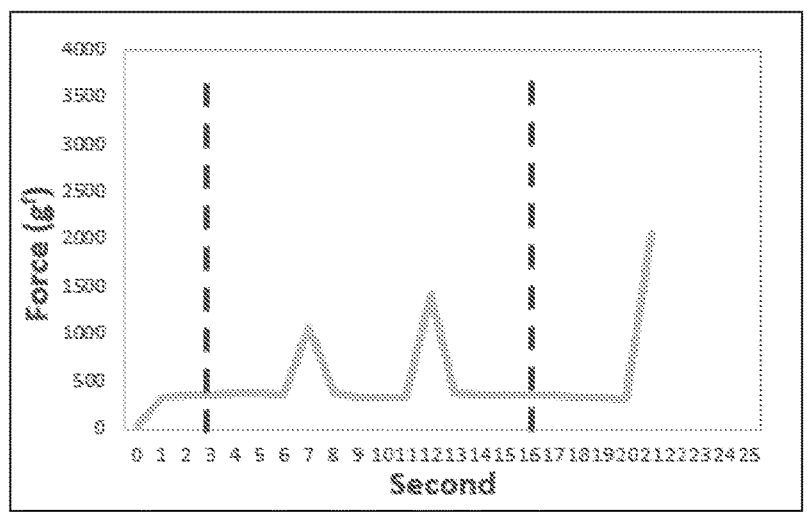
FIG. 6 shows a graph of the syringeability force ($g^f$) required to dispense 0.3 mL of a pharmaceutical suspension, prepared according to the disclosed methods, through a 33-gauge ½ inch needle. As indicated by the dashed red lines, readings were taken from 3-16 seconds to determine an appropriate endpoint of sonication.
Figure 7:
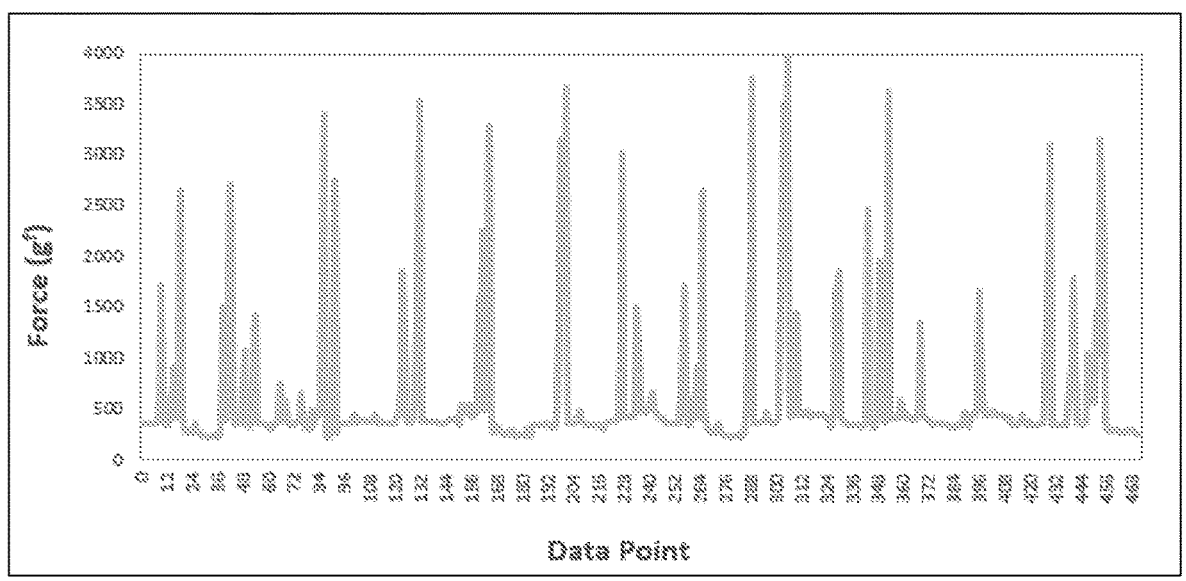
FIG. 7 shows the combined syringeability force results obtained from an analysis of a TA suspension prepared according to the disclosed methods. The data is a combination of the 10 readings/s from the texture analyzer repeated over 15 syringeability force analyses.

Only readings from the $3^{rd}$ second to the $16^{th}$ second were utilized for this analysis to ensure break force (initial force to move the syringe) and end of dispensing readings were not included. Specifically, for each sample, 130 force data points (10 points/second from 3 to 16 seconds) for each of the fifteen tests (five each in the case of top, middle and bottom sampling) were combined for a total of 1950 force data points (see FIGS. 6 and 7). FIG. 6 provides a sample output of an exemplary analysis.

Figure 8:
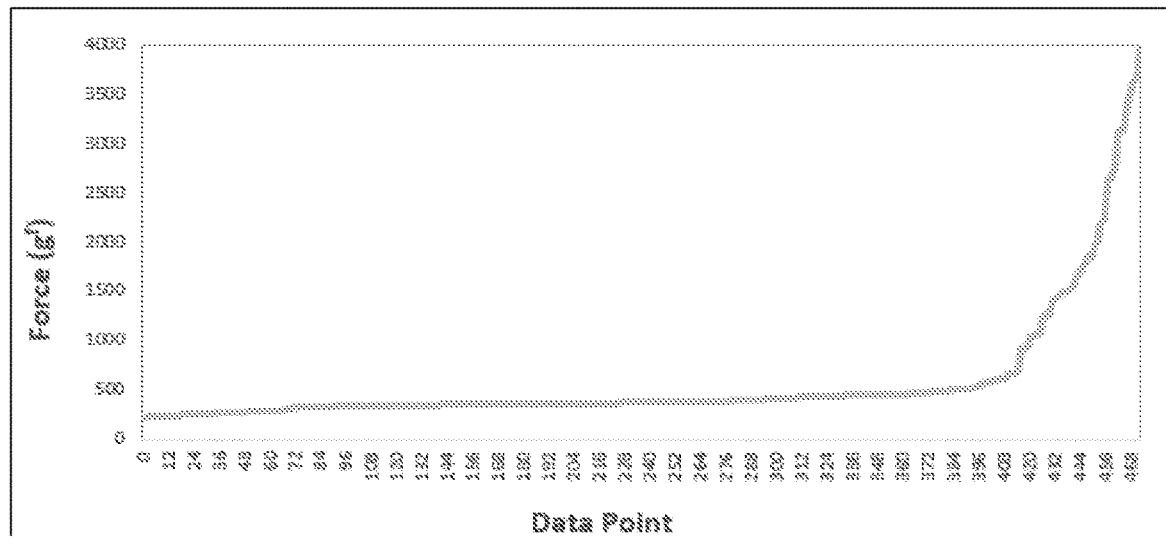
FIG. 8 shows the sorted syringeability force results obtained from an analysis of a TA suspension prepared according to the disclosed methods. The data is obtained by sorting the combination of the 10 readings/s from the texture analyzer repeated over 15 syringeability force analyses.

The obtained data were sorted in order so that the lowest result is first and the highest result is last. This may be performed in Excel or other suitable software (see FIG. 8).

Figure 9:
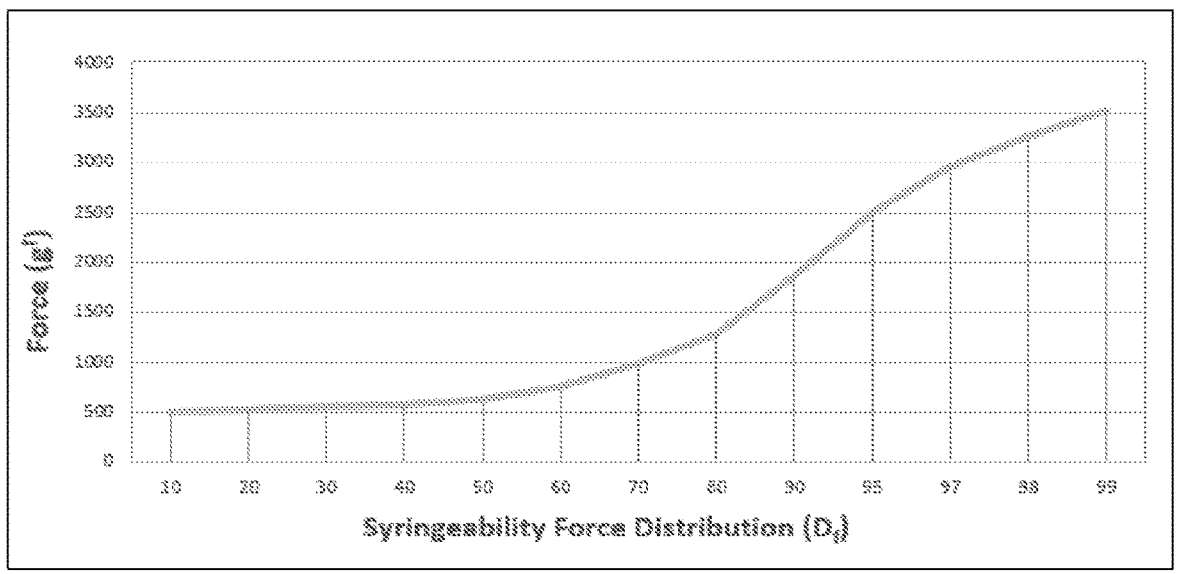
FIG. 9 shows the calculated syringeability force distribution based on the force required to dispense a 0.3 ml sample of TA suspension prepared according to the disclosed methods through a 33 gauge ½ inch needle.

The Syringeability Force Distribution ($D_f$) values provided herein combine readings from at least 15 Syringeability Force analyses, sorted from lowest to highest force to determine force value each % distribution. In a sorted list from smallest to greatest force over the 1950 force data points (for example) this corresponds to the 1755th data point (see FIG. 9).

FIGS. 6-9 provide results for combined syringeability force results, sorted syringeability force results and Syringeability Force Distribution ($D_f10=10\%$, $D_f20=20\%$, to $D_f99=99\%$ distribution), respectively.

Example 5: Determination of Sonication Endpoint

Syringeability force distribution (DO is used to evaluate the product quality attribute of the sonicated product. The end point of sonication is defined as when additional sonication has minimal-to-no-effect on the syringeability force distribution.

The three DOE studies evaluated the change in syringeability force at various distributions, e.g. Df90, Df95, etc. over sonication time. The distribution was used to determine the sonication time required to ensure the sonication process consistently achieved the end point of sonication. A syringeability force at 90% distribution (Df90) was selected to establish a limit for the sonication endpoint.

Background: Qualitative syringeability analysis was performed at the end of sonication to confirm that 0.3 ml of the suspension product could be dispensed through a 33G'½" needle using slight to minimum force to achieve a steady flow without clogging.

To establish a quantitative method, a Texture Analyzer was utilized to measure the force required to dispense the suspension product at a constant flow. Utilization of the Texture Analyzer method provided a discriminating approach to measure the syringeability force distribution at various sonication times to determine the end point of sonication.

Figure 10:
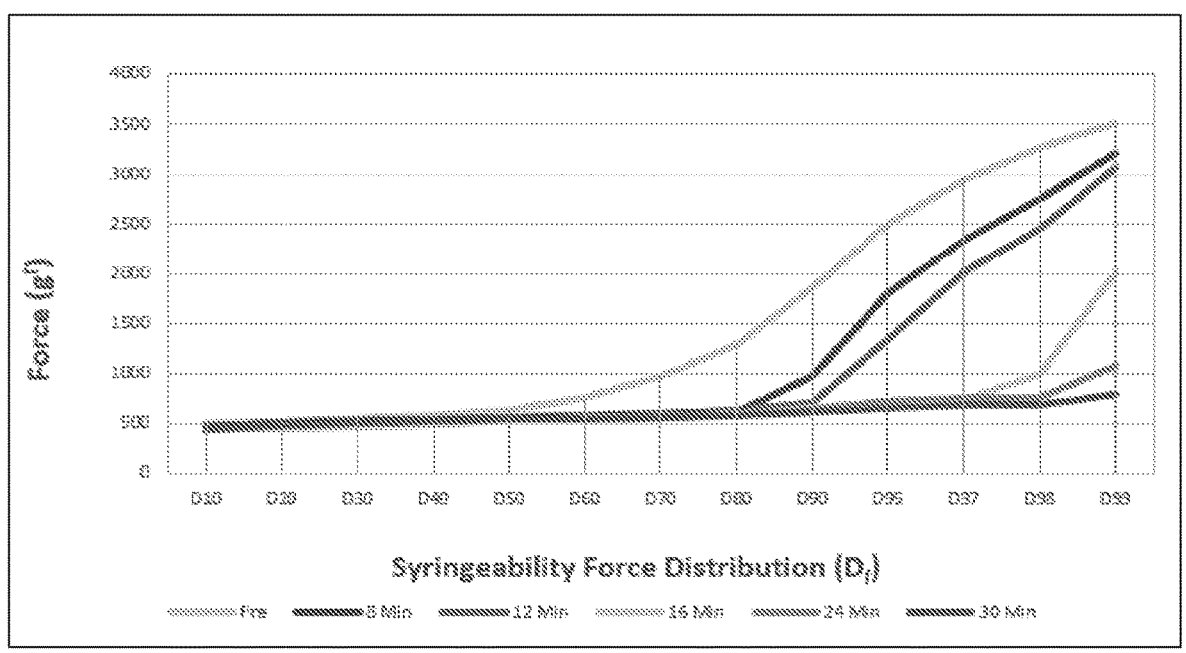
FIG. 10 shows syringeability force distribution results from a Design of Experiments study.

The design of experiments (DOE) results shown in FIG. 10 (summarized in Table 7, below) show that there were minimal changes to 90% of syringeability results after 16 minutes of sonication. Therefore, a specification limit of $D_f90=NMT$ 760 $g^f$ was determined as the endpoint of sonication. Process sonication time was set at 16 minutes.

TABLE 7

Summary of DOE Experiments

| | Pre-Sonication | 8 mins | 12 mins | 16 mins | 24 mins | 30 mins |
|---|---|---|---|---|---|---|
| $D_f10$ | 503 | 445.4 | 483 | 434.3 | 449 | 458.7 |
| $D_f20$ | 528 | 477.4 | 517 | 457 | 477 | 494.5 |
| $D_f30$ | 556 | 510.7 | 534 | 481.3 | 510 | 513.9 |
| $D_f40$ | 582 | 532.5 | 549 | 502.1 | 534 | 529.1 |
| $D_f50$ | 632 | 543.8 | 567 | 527.3 | 552 | 541.5 |
| $D_f60$ | 762 | 561 | 586 | 545.9 | 565 | 553.4 |
| $D_f70$ | 977 | 586.3 | 607 | 566.5 | 581 | 566.7 |
| $D_f80$ | 1291 | 619.8 | 640 | 595.4 | 606 | 589.5 |
| $D_f90$ | 1863 | 989 | 709 | 659.1 | 645 | 620.9 |
| $D_f95$ | 2508 | 1808.4 | 1342 | 724.7 | 729 | 657.4 |
| $D_f99$ | 3522 | 3220.3 | 3085 | 2014.4 | 1086 | 792.2 |

Example 6: Syringeability for TA Suspension of the Present Disclosure

The syringeability of a particulate- and aggregate-free TA injectable suspension (40 mg/mL) through a 30 gauge and 33 gauge needle was evaluated. It was determined that the suspensions of the present disclosure (about 150 µL) could be injected through a 30 gauge and 33 gauge needle without clogging.

Example 7: Redispersability of TA Injectable Suspension of the Present Disclosure A method for analyzing the redispersability of a TA injectable suspension of the present disclosure was conducted (see below) and it was determined that the suspensions were redisperable.

Method: After 10 seconds of vigorous agitation, microscopic analysis of the agitated suspension indicates a homogenous suspension that was visually dispersed and essentially free of aggregates.

Example 8: Evaluation of Stability for a Particulate- and Aggregate-Free TA Suspension of the Present Disclosure The stability of particulate- and aggregate free TA suspension of the present disclosure was evaluated by monitoring appearance and testing the syringeability of the suspension after the material was stored for three months at 40° C./75% RH.

The suspension met the acceptance criteria for both appearance (i.e., no visible foreign particulate matter) and syringeability (i.e., 100 µL of the suspension was injectable through a 30 gauge needle without plugging) indicating that the suspension was stable for at least three months under accelerated stability conditions (i.e., 40° C./75% RH) (data not shown).

Numbered Embodiments of the Present Disclosure

1. A pharmaceutical suspension comprising:
   (a) about 40 mg/mL of triamcinolone acetonide; and
   (b) a wetting agent;
   wherein the composition is essentially particulate-free and aggregate-free.
2. A pharmaceutical suspension comprising:
   (a) about 40 mg/mL of triamcinolone acetonide;
   (b) a wetting agent;

wherein the injection of the suspension through a 30-gauge needle of 900 μm to 1100 μm length provides an average glide force of less than about 1.00 Newton.
3. The suspension of embodiment 1 or 2, wherein the triamcinolone acetonide particles have a $D_{10}$ of less than about 3.0 μm, less than about 2.5 μm, less than about 2.0 μm, less than about 1.5 μm, less than about 1.0 μm, or less than about 0.5 μm.
4. The suspension of embodiment 1 or 2, wherein the triamcinolone acetonide particles have a $D_{50}$ of less than about 7.0 μm, less than about 6.0 μm, less than about 5.0 μm, less than about 4.0 μm, or less than about 3.0 μm.
5. The suspension of embodiment 1 or 2, wherein the triamcinolone acetonide particles have a $D_{90}$ of less than about 12.0 μm, less than about 11.0 μm, less than about 10.0 μm, less than about 9.0 μm, less than about 8.0 μm, less than about 7.0 μm, or less than about 5.0 μm.
6. The suspension of any one of embodiments 1-5, wherein the suspension is essentially particulate-free as determined by the visual inspection methods described in USP <790>.
7. The suspension of any one of embodiments 1-6, wherein the suspension is essentially particulate-free as determined by the visual inspection methods described in USP <1790>.
8. The suspension of any one of embodiments, 1-7, wherein essentially particulate-free and aggregate-free is characterized by having essentially no particulates or aggregates greater than about 50 μm, greater than about 45 μm, greater than about 40 μm, greater than about 35 μm, greater than about 30 μm, greater than about 25 μm, greater than about 20 μm, greater than about 15 μm, greater than about 10 μm, or greater than about 5 μm.
9. The suspension of any one of embodiments, 1-8, wherein essentially particulate-free and aggregate-free is characterized by having essentially no particulates or aggregates greater than about 50 μm.
10. The suspension of any one of embodiments, 1-9, wherein essentially particulate-free and aggregate-free is characterized by having essentially no particulates or aggregates greater than about 30 μm.
11. The suspension of any one of embodiments, 1-10, wherein essentially particulate-free and aggregate-free is characterized by having essentially no particulates or aggregates greater than about 10 μm.
12. The suspension of any one of embodiments 1-11, wherein the suspension is aggregate-free as determined by a Syringeability Force Test.
13. The suspension of any one of embodiments 1-12, wherein the Syringeability Force Distribution ($D_f90$) of the suspension is not more than about 760 $g^f$.
14. The suspension of any one of embodiments 1-13, wherein the composition comprises about 0.02% w/v of the wetting agent.
15. The suspension of any one of embodiments 1-14, wherein the injection of the suspension through a 30-gauge needle of 900 μm to 1100 μm length provides an average glide force of less than about 0.9 N, about 0.8 N or about 0.7 N.
16. The suspension of any one of embodiments 1-15, wherein the wetting agent is polysorbate 80.
17. The suspension of any one of embodiments 1-16, further comprising one or more isotonicity agents and one or more viscosity agents.
18. The suspension of embodiment 17, wherein the one or more isotonicity agents comprises sodium chloride, potassium chloride, calcium chloride, and magnesium chloride.
19. The suspension of any one of embodiments 1-18, further comprising one or more viscosity agents.
20. The suspension of embodiment 19, wherein the viscosity agent is carboxymethylcellulose sodium.
21. A pharmaceutical suspension prepared by a process comprising:
    (a) providing an essentially particulate-free first solution comprising one or more viscosity agents, one or more one tonicity agents, and one or more pH buffer agents in an aqueous solvent;
    (b) providing an essentially particulate-free second solution comprising one or more wetting agents in an aqueous solvent;
    (c) adding triamcinolone acetonide particles having a $D_{50}$ of less than about 5 μm to the solution of Step (b) to provide a suspension;
    (d) adding the suspension of Step (c) to the solution of Step (a); and
    (e) sonicating the suspension of Step (d), wherein the suspension comprises about 40 mg/mL of triamcinolone acetonide.
22. The suspension of embodiment 21, wherein the sonication Step (e) is conducted until the suspension is essentially aggregate-free.
23. The suspension of embodiment 21, wherein the sonication Step (e) is conducted until the suspension is essentially aggregate-free as determined by the Syringeability Force Test.
24. The suspension of embodiment 21, wherein the sonication Step (e) is conducted until the Syringeability Force Distribution ($D_f90$) of the suspension is not more than about 760 $g^f$.
25. The suspension of any one of embodiments, 21-24, wherein essentially aggregate-free is characterized by having essentially no aggregates greater than about 50 μm, greater than about 45 μm, greater than about 40 μm, greater than about 35 μm, greater than about 30 μm, greater than about 25 μm, greater than about 20 μm, greater than about 15 μm, greater than about 10 μm, or greater than about 5 μm.
26. The suspension of any one of embodiments, 21-25, wherein essentially aggregate-free is characterized by having essentially no aggregates greater than about 50 μm.
27. The suspension of any one of embodiments, 21-26, wherein essentially aggregate-free is characterized by having essentially no aggregates greater than about 30 μm.
28. The suspension of any one of embodiments, 21-27, wherein essentially aggregate-free is characterized by having essentially no aggregates greater than about 10 μm.
29. The suspension of any one of embodiments 21-28, further comprising filtering the sonication suspension of Step (e).
30. The suspension of embodiment 29, wherein the suspension of Step (e) is filtered through a 234 μm pore size filter.

31. The suspension of any one of embodiments 21-30, wherein the essentially particulate-free first solution is provided by:
   (a) filtering a solution comprising one or more viscosity agents;
   (b) filtering a solution comprising one or more one tonicity agents, and one or more pH buffer agents in an aqueous solvent; and
   (c) combining the solutions of Step (a) and Step (b) to provide the essentially particulate-free first solution.
32. The suspension of any one of embodiments 21-31, wherein the essentially particulate-free second solution is provided by filtering a solution comprising one or more wetting agents in an aqueous solvent to provide the essentially particulate-free first solution.
33. The suspension of embodiment 31 or 32, wherein the solutions are filtered through a 0.20 μm pore size filter.
34. The suspension of embodiment 21-33, wherein the wetting agent is polysorbate 80.
35. The suspension of embodiment 34, wherein the suspension comprises about 0.02% w/v polysorbate 80.
36. The suspension of any one of embodiments 21-35, wherein the one or more tonicity agents comprises sodium chloride, potassium chloride, calcium chloride, and magnesium chloride.
37. The suspension of any one of embodiments 21-36, wherein the viscosity agent is carboxymethylcellulose sodium.
38. A pharmaceutical suspension prepared by a process comprising:
   (a) heating a mixture of one or more wetting agents, one or more one tonicity agents, one or more pH buffer agents and triamcinolone acetonide particles having a $D_{50}$ of less than about 5 μm in an aqueous solvent;
   (b) cooling the suspension of Step (a);
   (c) adding an aqueous solution of one or more viscosity agents to the suspension of Step (b);
   (d) stirring the suspension of Step (c) at a low-shear stirring rate; and
   (e) sonicating the suspension of Step (d), wherein the suspension comprises about 40 mg/mL of triamcinolone acetonide.
39. The suspension of embodiment 38, wherein the wetting agent is polysorbate 80.
40. The suspension of embodiment 39, wherein the suspension comprises about 0.02% w/v polysorbate 80.
41. The suspension of any one of embodiments 38-40, wherein the one or more tonicity agents comprises sodium chloride, potassium chloride, calcium chloride, and magnesium chloride.
42. The suspension of any one of embodiments 38-41, wherein the viscosity agent is carboxymethylcellulose sodium.
43. The suspension of any one of embodiments 38-42, wherein the mixture of step (a) is heated to about 120° C. for about 15 minutes.
44. The suspension of any one of embodiments 38-43, wherein the low-shear stirring rate is from about 60 rpm to about 120 rpm.
45. The suspension of any one of embodiments 38-44, further comprising filtering the aqueous solution of the viscosity agent prior to step (c).
46. The suspension of any one of embodiments 1-45, wherein the viscosity of the suspension is about 10 cPs.
47. The suspension of any one of embodiments 1-46, wherein the degree of flocculation of the suspension is from about 15 to about 20.
48. The suspension of embodiment 47, wherein the degree of flocculation of the suspension is about 17.
49. The suspension of any one of embodiments 1-48, wherein less than about 70% of the particles are settled after about 8 h as determined by the Settling Test.
50. The suspension of any one of embodiments 1-49 wherein the suspension comprises:

| | |
|---|---|
| Triamcinolone acetonide | 40 mg/mL |
| Sodium chloride | 0.55% w/v |
| Carboxymethylcellulose sodium | 0.5% w/v |
| Polysorbate 80 | 0.02% w/v |
| Potassium chloride | 0.075% w/v |
| Calcium chloride dihydrate | 0.048% w/v |
| Magnesium chloride hexahydrate | 0.03% w/v |
| Sodium acetate trihydrate | 0.39% w/v |
| Sodium citrate dihydrate | 0.17% w/v |

51. A kit comprising:
   (a) a suspension of any one of embodiments 1-50 in a suitable container and
   (b) a suspension delivery system for suprachoroidal injection of the suspension.
52. The kit of embodiment 51, wherein the suitable container is a glass vial.
53. The kit of embodiment 52, wherein the glass vial contains about 0.9 mL of the suspension.
54. The kit of any one of embodiments 51-53, wherein the suspension delivery system comprises a syringe and at least one microneedle.
55. The kit of embodiment 54, wherein the diameter of the microneedle is about 30 gauge.
56. The kit of any one of embodiments 51-55, wherein the length of the microneedle is selected from 900 μm and 1100 μm.
57. The kit of any one of embodiments 51-56, comprising:
   (a) a suspension of any one of embodiments 1-50 packaged in a glass vial,
   (b) a vial adaptor, and
   (c) a suspension delivery system comprising
      (i) a syringe,
      (ii) a 30 gauge microneedle of 900 μm length and
      (iii) a 30 gauge microneedle of 1100 μm length.
58. A packaged product comprising a suspension of any one of embodiments 1-50 in a suitable container.
59. The packaged product of embodiment 58, wherein the suitable container is filled with about 0.9 mL of the suspension.
60. The packaged product of embodiment 59, wherein the packaged product contains a consistent weight of triamcinolone acetonide as indicated by the packaged product having a content uniformity that meets the requirements of the USP <905> Uniformity of Dosage Units test.
61. The packaged product of any one of embodiments 58-60, wherein the packaged product contains a consistent assay of triamcinolone acetonide as indicated by the packaged product having an assay of about 90.0% to about 110.0% (by weight) of the product label embodiment as determined by high performance liquid chromatography.
62. A method of treating macular edema in a patient in need thereof comprising administering a therapeutically effective amount of the suspension of any one of embodiments 1-47 to the posterior region of the patient's eye, wherein the suspension is administered by suprachoroidal injection.

63. The method of embodiment 62, wherein the macular edema is selected from macular edema associated with retinal vein occlusion, macular edema associated with non-infectious uveitis and diabetic macular edema.

64. A process for preparing a pharmaceutical suspension comprising:
  (a) providing an essentially particulate-free first solution comprising one or more viscosity agents, one or more one tonicity agents, and one or more pH buffer agents in an aqueous solvent;
  (b) providing an essentially particulate-free second solution comprising one or more wetting agents in an aqueous solvent;
  (c) adding triamcinolone acetonide particles having a $D_{50}$ of less than about 5 µm to the solution of Step (b) to provide a suspension;
  (d) adding the suspension of Step (c) to the solution of Step (a); and
  (e) sonicating the suspension of Step (d), wherein the suspension comprises about 40 mg/mL of triamcinolone acetonide.

65. The process of embodiment 64, wherein the sonication Step (e) is conducted until the suspension is essentially aggregate-free.

66. The process of embodiment 65, wherein the sonication Step (e) is conducted until the suspension is essentially aggregate-free as determined by a Syringeability Force Test.

67. The process of embodiment 66, wherein the sonication Step (e) is conducted until the Syringeability Force Distribution ($D_f 90$) of the suspension is not more than about 760 g.

68. The process of any one of embodiments 64-67, further comprising filtering the sonication suspension of Step (e).

69. The suspension of embodiment 68, wherein the suspension of Step (e) is filtered through a 234 µm pore size filter.

70. A process for preparing a pharmaceutical suspension comprising:
  (a) heating a mixture of one or more wetting agents, one or more tonicity agents, one or more pH buffer agents and triamcinolone acetonide having a $D_{50}$ of less than about 5 µm in an aqueous solvent;
  (b) cooling the suspension of Step (a);
  (c) adding an aqueous solution of one or more viscosity agents to the suspension of Step (b);
  (d) stirring the suspension of Step (c) at a low-shear stirring rate; and
  (e) sonicating the suspension of Step (d), wherein the suspension comprises about 40 mg/mL of triamcinolone acetonide.

71. The process of embodiment 70, wherein the wetting agent is polysorbate 80.

72. The process of embodiment 71, wherein the suspension comprises about 0.02% w/v polysorbate 80.

73. The process of any one of embodiments 70-72, wherein the one or more tonicity agent comprises sodium chloride, potassium chloride, calcium chloride, and magnesium chloride.

74. The process of any one of embodiments 70-73, wherein the viscosity agent is carboxymethylcellulose sodium.

75. The process of any one of embodiments 70-74, wherein the mixture of step (a) is heated to about 120° C. for about 15 minutes.

76. The process of any one of embodiments 70-75, wherein the low-shear stirring rate is from about 60 to about 120 rpm.

77. The process of any one of embodiments 70-76, further comprising filtering the aqueous solution of the viscosity agent prior to step (c).

78. The process of embodiment 77, wherein the aqueous solution of the viscosity agent is filtered through a polyether sulfone filter membrane.

79. The process of any one of embodiments 70-78, further comprising filling about 0.9 mL of the suspension of step (e) into a suitable container to provide a packaged product.

80. The process of embodiment 79, wherein the filling provides a packaged product with a consistent weight of triamcinolone acetonide as indicated by the packaged product having a content uniformity that meets the requirements of the USP <905> Uniformity of Dosage Units test.

81. The process of embodiment 79 or 80, wherein the filling provides a packaged product with consistent assay of triamcinolone acetonide as indicated by the packaged product having an assay of about 90.0% to about 110.0% (by weight) of the product label embodiment as determined by high performance liquid chromatography.

82. The process of any one of embodiments 79-81, wherein the suitable container is a glass vial that is filled using a piston drive or peristaltic pump system.

What is claimed is:

1. A pharmaceutical suspension comprising:
  (a) about 40 mg/mL of triamcinolone acetonide; and
  (b) a wetting agent;
  wherein the suspension is essentially particulate-free and aggregate-free,
  wherein the triamcinolone acetonide particles have a $D_{50}$ of less than about 3.0 µm; and
  wherein the viscosity of the suspension is about 5 cPs to about 20 cPs.

2. The suspension of claim 1, wherein the triamcinolone acetonide particles have a $D_{10}$ of less than about 2.0 µm.

3. The suspension of claim 1, wherein the triamcinolone acetonide particles have a $D_{90}$ of less than about 7.0 µm.

4. The suspension of claim 1, wherein the suspension is essentially particulate-free as determined by the visual inspection methods described in USP <790>.

5. The suspension of claim 1, wherein the suspension is essentially particulate-free as determined by destructive sample preparation and the visual inspection methods described in USP <1790>.

6. The suspension of claim 1, wherein the suspension is essentially aggregate-free as determined by a Syringeability Force Test.

7. The suspension of claim 1, wherein the Syringeability Force Distribution ($D_f 90$) of the suspension is not more than about 760 $g^f$.

8. The suspension of claim 1, wherein the suspension comprises about 0.02% w/v of the wetting agent.

9. The suspension of claim 1, wherein the wetting agent is polysorbate 80.

10. The suspension of claim 1, further comprising one or more isotonicity agents and one or more viscosity agents.

11. The suspension of claim 10, wherein the one or more isotonicity agents comprise sodium chloride, potassium chloride, calcium chloride, and magnesium chloride.

12. The suspension of claim 10, wherein the viscosity agent is carboxymethylcellulose sodium.

13. The suspension of claim 1, wherein after 10 seconds of vigorous agitation, microscopic analysis of the agitated suspension indicates a homogenous suspension that is visually dispersed and is essentially free of aggregates.

14. The suspension of claim 1, wherein the viscosity of the suspension is about 10 cPs.

15. The suspension of claim 1, wherein less than about 70% of the particles are settled after about 8 h as determined by the Settling Test.

16. The suspension of claim 1, wherein the suspension comprises 40 mg/mL of triamcinolone acetonide, 0.55% w/v of sodium chloride, 0.5% w/v of carboxy methylcellulose sodium, 0.02% w/v of polysorbate 80, 0.075% w/v of potassium chloride, 0.048% w/v of calcium chloride dihydrate, 0.03% w/v of magnesium chloride hexahydrate, 0.39% w/v of sodium acetate trihydrate, and 0.17% w/v of sodium citrate dihydrate.

17. A method of treating macular edema in a patient in need thereof comprising administering a therapeutically effective amount of the suspension of claim 1 to the posterior region of the patient's eye, wherein the suspension is administered by suprachoroidal injection.

18. A process for preparing a pharmaceutical suspension comprising:
(a) providing an essentially particulate-free first solution comprising one or more viscosity agents, one or more one tonicity agents, and one or more pH buffer agents in an aqueous solvent;
(b) providing an essentially particulate-free second solution comprising one or more wetting agents in an aqueous solvent;
(c) adding triamcinolone acetonide particles having a $D_{70}$ of less than about 5 µm to the solution of Step (b) to provide a suspension;
(d) adding the suspension of Step (c) to the solution of Step (a); and
(e) sonicating the suspension of Step (d),
wherein the suspension comprises about 40 mg/mL of triamcinolone acetonide.

19. A process for preparing a pharmaceutical suspension comprising:
(a) heating a mixture of one or more wetting agents, one or more tonicity agents, one or more pH buffer agents and triamcinolone acetonide having a $D_{50}$ of less than about 3 µm in an aqueous solvent to provide a suspension;
(b) cooling the suspension of Step (a);
(c) adding an aqueous solution of one or more viscosity agents to the suspension of Step (b);
(d) stirring the suspension of Step (c) at a low-shear stirring rate; and
(e) sonicating the suspension of Step (d),
wherein the suspension comprises about 40 mg/mL of triamcinolone acetonide.

20. A pharmaceutical suspension prepared by the process of claim 18.

21. The process of claim 18, wherein a filtering step provides the essentially particulate-free first solution and the essentially particulate-free second solution.

22. The process of claim 21, wherein the filter has a pore size of 0.1 µm to 0.5 µm.

23. The suspension of claim 1, wherein the triamcinolone acetonide particles have a $D_{50}$ of about 2.0 µm to about 2.5 µm.

24. A pharmaceutical suspension comprising:
(a) about 40 mg/mL of triamcinolone acetonide; and
(b) a wetting agent;
wherein the suspension is essentially particulate-free and aggregate-free;
wherein the viscosity of the suspension is about 5 cPs to about 20 cPs; and wherein the triamcinolone acetonide particles have a $D_{10}$ of less than about 2.0 µm, a $D_{50}$ of less than about 3.0 µm, and a $D_{90}$ of less than about 7.0 µm.

25. The pharmaceutical suspension of claim 24, wherein the viscosity of the suspension is about 6 cPs to about 12 cPs.

26. The pharmaceutical suspension of claim 25, wherein the viscosity of the suspension is about 10 cPs.

* * * * *